(12) United States Patent
Katsumata

(10) Patent No.: US 9,943,282 B2
(45) Date of Patent: Apr. 17, 2018

(54) IMAGE PROCESSING APPARATUS, IMAGE PROCESSING METHOD, AND IMAGE PROCESSING SYSTEM

(71) Applicant: CANON KABUSHIKI KAISHA, Tokyo (JP)

(72) Inventor: Shinya Katsumata, Kawasaki (JP)

(73) Assignee: Canon Kabushiki Kaisha, Tokyo (JP)

( * ) Notice: Subject to any disclaimer, the term of this patent is extended or adjusted under 35 U.S.C. 154(b) by 152 days.

(21) Appl. No.: 15/190,514

(22) Filed: Jun. 23, 2016

(65) Prior Publication Data
US 2017/0000443 A1      Jan. 5, 2017

(30) Foreign Application Priority Data

Jun. 30, 2015   (JP) ................................ 2015-132179

(51) Int. Cl.
| | | |
|---|---|---|
| *G06K 9/00* | (2006.01) | |
| *A61B 6/00* | (2006.01) | |
| *G06T 5/00* | (2006.01) | |
| *G06T 5/50* | (2006.01) | |

(52) U.S. Cl.
CPC .......... *A61B 6/5282* (2013.01); *A61B 6/4291* (2013.01); *A61B 6/5205* (2013.01); *G06T 5/002* (2013.01); *G06T 5/008* (2013.01); *G06T 5/50* (2013.01); *G06T 2207/10116* (2013.01)

(58) Field of Classification Search
None
See application file for complete search history.

(56) References Cited

U.S. PATENT DOCUMENTS

| | | | |
|---|---|---|---|
| 8,064,676 B2 | 11/2011 | Li | |
| 2003/0072417 A1* | 4/2003 | Kaufhold | A61B 6/482 378/207 |
| 2005/0002550 A1* | 1/2005 | Jabri | G06T 11/005 382/131 |
| 2008/0002807 A1* | 1/2008 | Debasish | A61B 6/00 378/7 |
| 2010/0104165 A1* | 4/2010 | Takahashi | G06T 5/002 382/132 |
| 2012/0008849 A1* | 1/2012 | Reboni | G06T 5/002 382/132 |
| 2012/0106697 A1* | 5/2012 | Carton | A61B 6/06 378/37 |
| 2014/0334700 A1* | 11/2014 | Yang | G06T 11/005 382/130 |

(Continued)

*Primary Examiner* — Shervin Nakhjavan
(74) *Attorney, Agent, or Firm* — Canon U.S.A., Inc. IP Division

(57) ABSTRACT

An image processing apparatus includes an estimation unit, a noise reduction unit, and an output unit. The estimation unit estimates a scattered-ray component contained in a radiation image acquired by irradiating an object with a radiation, wherein the scattered-ray component originates from a scattered ray which is a radiation scattered in the object. The noise reduction unit reduces a noise component included in the radiation image in accordance with first noise information obtained from the radiation image and second noise information obtained from a scattered-ray reduction image obtained by reducing the scattered-ray component from the radiation image. The output unit outputs a correction image obtained by reducing the scattered-ray component and the noise component in the radiation image.

21 Claims, 15 Drawing Sheets

(56) References Cited

U.S. PATENT DOCUMENTS

2015/0317771 A1* 11/2015 Kato .................... A61B 6/5205
382/132
2016/0140721 A1* 5/2016 Kawamura ............ A61B 6/466
382/132

* cited by examiner

IMAGE PROCESSING APPARATUS, IMAGE PROCESSING METHOD, AND IMAGE PROCESSING SYSTEM

BACKGROUND OF THE INVENTION

Field of the Invention

The present invention relates to an image processing apparatus which performs image processing on a radiation image, an image processing method, and an image processing system.

Description of the Related Art

A radiation image obtained by irradiating an object with a radiation includes a component of primary radiation which travels straight from a radiation source and a component of a scattered ray which is a radiation scattered in the object, and further includes a noise component. Such a scattered-ray component may cause degradation of contrast of a radiation image. Furthermore, the noise component may cause degradation of image quality of the radiation image.

In recent years, a method for reducing a scattered-ray component and a noise component from the radial image by image processing has been proposed. U.S. Pat. No. 8,064,676 discloses a technique of reducing a scattered-ray component which is seen to be dominant in pixels of high luminance in a low frequency band and a noise component which is seen to be dominant in pixels of low luminance in a high frequency band in accordance with a frequency and a luminance value of a radiation image.

So-called noise includes quantum noise derived from statistical fluctuation in positions and density of X-ray photons detected by a radiation detector as a result of a random phenomenon of the X-ray photons. The quantum noise approximately correlates with the dose of radiation which has reached the radiation detector. In a method in which a scattered-ray component reduction process and a noise reduction process are individually performed in accordance with a frequency and a luminance value of a radiation image, accuracy of reduction of a noise component may be deteriorated since the correlation between an amount of a scattered ray which has reached a radiation detector and a generated noise amount is not taken into consideration.

SUMMARY OF THE INVENTION

According to some embodiments of the present invention, an image processing apparatus includes an estimation unit configured to estimate a scattered-ray component contained in a radiation image acquired by irradiating an object with a radiation, wherein the scattered-ray component originates from a scattered ray which is a radiation scattered in the object, a noise reduction unit configured to reduce a noise component included in the radiation image in accordance with first noise information obtained from the radiation image and second noise information obtained from a scattered-ray reduction image obtained by reducing the scattered-ray component from the radiation image, and an output unit configured to output a correction image obtained by reducing the scattered-ray component and the noise component in the radiation image.

Further features of the present invention will become apparent from the following description of exemplary embodiments with reference to the attached drawings.

DESCRIPTION OF THE EMBODIMENTS

Figure 1:
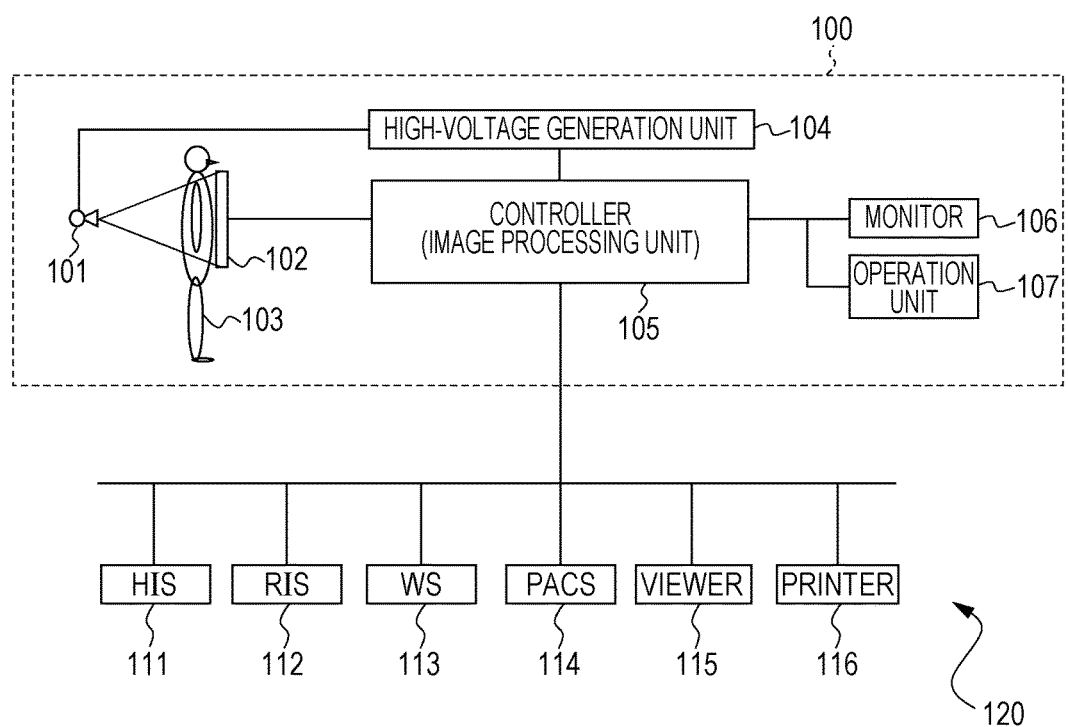
FIG. 1 is a diagram illustrating a configuration of an information system including an image processing apparatus according to an embodiment of the present invention.

An image processing apparatus and an information system 120 including a radiographic system 100 according to an embodiment of the present invention will be described with reference to FIG. 1. The image processing apparatus of this embodiment corresponds to a controller 105 included in the radiographic system 100. The controller 105 is referred to as an "image processing apparatus 105" where appropriate since image processing according to the embodiment of the present invention is described hereinafter. The information system 120 manages information before and after capturing of a radiation image, and includes a hospital information system (HIS) 111, a radiography information system (RIS) 112, a work station (WS) 113, a picture archiving-and-communication system (PACS) 114, a viewer 115, and a printer 116. The HIS 111 integrally manages patient information and diagnosis information including examination performed by radiography. The RIS 112 manages order of the radiography. The WS 113 is an image processing terminal which performs image processing on a radiation image captured by the radiographic system 100. The WS 113 may be replaced by at least one computer in which software having a function similar to that of the WS 113 is installed. The PACS 114 is a database system which stores images obtained by radiography in the information system 120 or other medical imaging apparatuses. The PACS 114 includes a storage unit (not illustrated) which stores medical images and attached information such as imaging conditions of the medical images and patient information and a controller (not illustrated) which manages information stored in the storage unit. The viewer 115 which is a terminal for image diagnosis reads an image stored in the PACS 114 or the like and displays the read image for diagnosis. The printer 116 is a film printer, for example, which outputs an image stored in the PACS 114 or the like on a film.

The radiographic system 100 of this embodiment uses an X-ray as a radial ray. The radiographic system 100 includes an X-ray source 101 which is an example of a radiation generating apparatus, a flat panel detector (FPD) 102, and the controller 105. The X-ray source 101, the FPD 102, and the controller 105 are connected to one another through a cable or a communication system. The controller 105 adds imaging conditions of imaging, patient information, and the like to a captured radiation image. The controller 105 adds the information to the radiation image in accordance with a standard of digital imaging and communications in medicine (DICOM) and generates a DICOM image file including data on the radiation image, the patient information, the imaging conditions, and the like. The controller 105 transmits the image to the WS 113 and the PACS 114. The order of the imaging is transmitted from the RIS 112 to the controller 105, for example. The controller 105 reads the imaging conditions from the storage unit (not illustrated) in accordance with the information input from the RIS 112.

The X-ray source 101 may be an X-ray tube or other arbitrary radiation sources suitable for obtainment of a medical image or other images. A high-voltage generation unit 104 supplies a high-voltage pulse to the X-ray source 101 when a user presses an exposure switch (not illustrated) and causes the X-ray source 101 to expose a region including an object 103 with an X-ray. The X-ray which is transmitted through the object 103 or a portion in the vicinity of the object 103 is incident on the FPD 102 serving as an X-ray detector. The FPD 102 converts the input X-ray into an electric signal and transmits the electric signal as a digital image to the controller 105 under control of the controller 105. For example, in the FPD 102, a fluorescent substance (not illustrated) converts the input X-ray into visible light, a photodiode (not illustrated) detects the visible light, and an A/D converter (not illustrated) converts the visible light into an electric signal. Alternatively, in the FPD 102, amorphous selenium (not illustrated) converts the X-ray into an electric signal. Pixel values of the radiation image are obtained from output of radiation detecting elements (not illustrated) included in the FPD 102. Each of the radiation detecting elements (not illustrated) includes the fluorescent substance (not illustrated) and the photodiode (not illustrated), for example. Alternatively, each of the radiation detecting elements (not illustrated) includes the amorphous selenium.

A digital signal is subjected to image processing in the controller 105 and the WS 113 and stored in the PACS 114 or the like. The units included in the information system 120 are at least connected to one another through a bus or other communication systems, and may be installed in remote locations.

Figure 2:
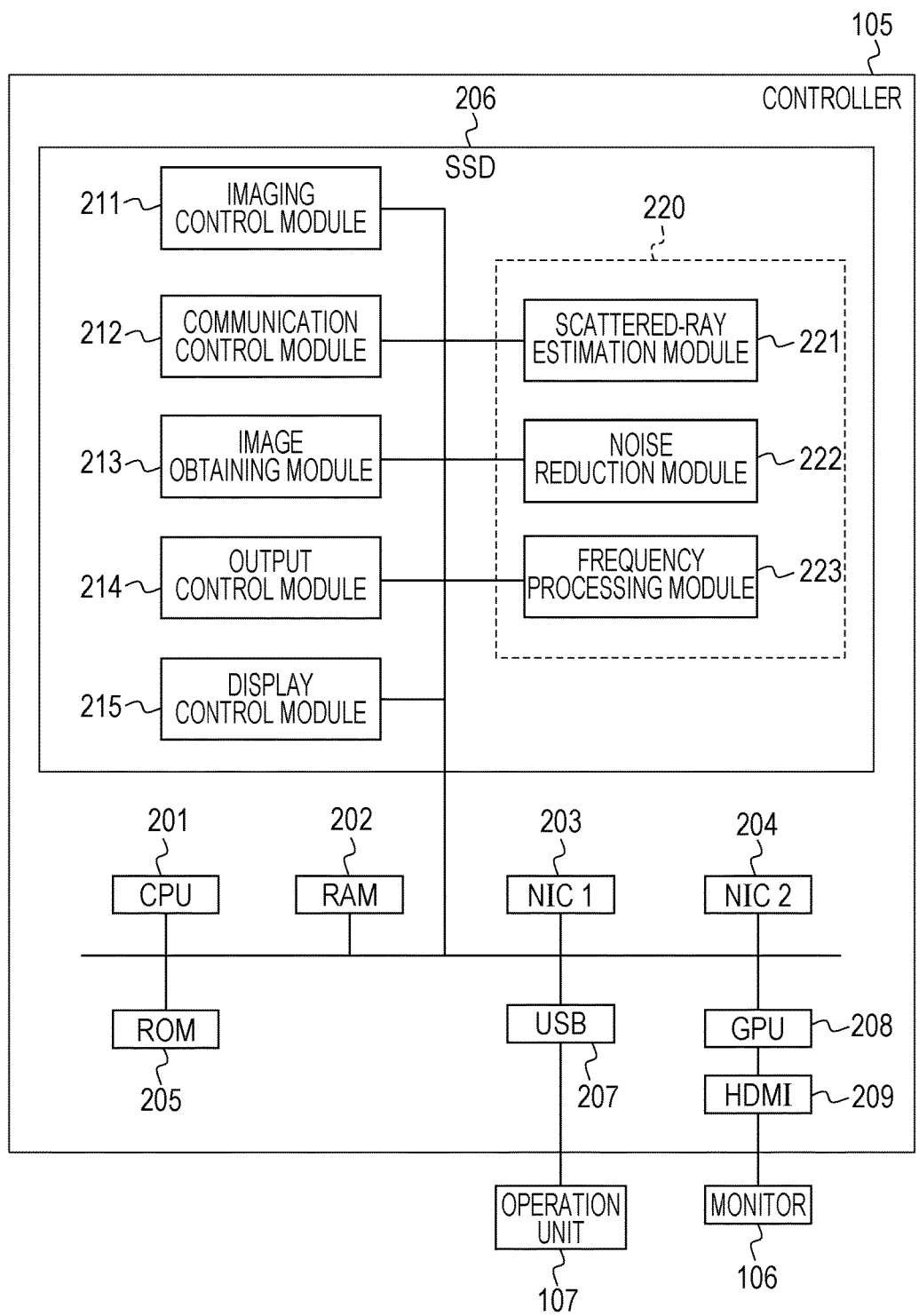
FIG. 2 is a diagram illustrating a configuration of the image processing apparatus according to the embodiment of the present invention.

Next, a configuration of the image processing apparatus according to this embodiment of the present invention will be described in detail with reference to FIG. 2. The image processing apparatus according to the embodiment of the present invention is the controller 105 connected to the information system 120 and is constituted by at least one computer. The computer constituting the controller 105 includes a central processing unit (CPU) 201 serving as a main controller, a random access memory (RAM) 202, a read only memory (ROM) 205, and a solid state drive (SSD) 206 which serve as storage units, a graphics processing unit (GPU) 208 serving as a graphic controller, network interface cards (NICs) 203 and 204 serving as communication units, a universal serial bus (USB) 207 serving as a connection unit, and a high definition multimedia interface (HDMI (registered trademark)) 209 which are connected to one another through an internal bus in a communication available manner. The CPU 201 is a control circuit which integrally controls the controller 105 and the units connected to the controller 105. The RAM 202 stores programs for executing processes performed by the controller 105 and the units connected to the controller 105 and various parameters to be used in image processing. Instructions included in the programs developed in the RAM 202 are successively executed by the CPU 201 so that image processing described below is realized. For example, the first NIC 203 serving as the communication unit is connected to an access point of a facility where radiography is performed, and the second NIC 204 is connected to an access point which relays communication in the information system 120. The SSD 206 stores the programs described above, radiation images obtained by imaging, attached information, and various parameters. The USB 207 is connected to an operation unit 107. The GPU 208 which is an image processing unit executes image processing under control of the CPU 201. An image obtained as a result of the image processing is output through the HDMI 209 to a monitor 106 and displayed on the monitor 106. The monitor 106 and the operation unit 107 may be integrated as a touch panel monitor.

Examples of the programs stored in the SSD 206 include an imaging control module 211, a communication control module 212, an image obtaining module 213, an output control module 214, a display control module 215, and an image processing module 220 which includes a scattered-ray estimation module 221, a noise reduction module 222, and a frequency processing module 223. These modules function by being executed by the CPU 201 or the GPU 208.

The imaging control module 211 is a program for integrally controlling execution of radiography. The imaging control module 211 reads the order transmitted from the RIS 112 so as to specify imaging conditions, and causes the communication control module 212 to transmit a signal requesting a state of the FPD 102. Note that the specifying of the imaging conditions may be performed by reading content of imaging conditions input by the user through the operation unit 107. Furthermore, the imaging control module 211 causes the communication control module 212 to transmit a signal requesting a state of the high-voltage generation unit 104.

The communication control module 212 controls communication through the first and second NICs 203 and 204. The communication control module 212 transmits a signal which brings the FPD 102 into an imaging available state to a communication unit (not illustrated) in accordance with control of the imaging control module 211 or an input from the operation unit 107. Furthermore, the communication control module 212 transmits, to the communication unit (not illustrated), a signal which brings the high-voltage generation unit 104 into a state in which the high-voltage generation unit 104 can generate a high-voltage pulse to the X-ray source 101 in accordance with the control of the imaging control module 211 or an input by the operation unit 107.

The image obtaining module 213 performs control of a process of obtaining an image to be used in the image processing according to the embodiment of the present invention. For example, the image obtaining module 213 causes the NIC 203 to receive a radiation image captured by the FPD 102. Note that reception of radiation images may be completed when data other than size-reduced images which have small data amounts among radiation images is received after the size-reduced images among the radiation images are preferentially received. Such a size-reduced image is obtained only using output signals selectively read from some elements by reading signals of a plurality of radiation detecting elements in even-numbered columns which give pixel values of a radiation image and which are included in the FPD 102. Alternatively, signals of some of the radiation detecting elements may be simultaneously read. A read image may be divided into a plurality of small regions and a size-reduced image may be constituted using representative values of the small regions. Alternatively, the NIC 203 may receive a radiation image stored in the PACS 114 or a storage unit (not illustrated) on a network. Moreover, a radiation image stored in the SSD 206 of the image processing apparatus 105 or other storage units (not illustrated) may be read.

The image processing module 220 performs image processing on a radiation image obtained by the image obtaining module 213. The image processing module 220 includes the scattered-ray estimation module 221, the noise reduction module 222, and the frequency processing module 223, for example. The image processing performed by the image processing module 220 includes general image processing in addition to processing performed by the scattered-ray estimation module 221, the noise reduction module 222, and the frequency processing module 223. The image processing module 220 is executed by the CPU 201, and the CPU 201 controls the GPU 208, and the GPU 208 executes the image processing. The image processing will be described later in detail.

The output control module 214 controls output of a correction image which has been subjected to the image processing performed by the image processing module 220 so that a scattered-ray component and a noise component are reduced. The output control module 214 outputs the correction image to the monitor 106 so that the monitor 106 displays the correction image, for example. Furthermore, the output control module 214 outputs the correction image to the PACS 114 and the printer 116 via the NIC 204, for example. By this, the PACS 114 stores the correction image and the printer 116 outputs the correction image onto a film or the like. Furthermore, the output control module 214 may output the correction image to a storage unit (not illustrated) inside or outside the controller 105 so as to store the correction image in the storage unit. Furthermore, the correction image is preferably output with various information based on the DICOM standard. A modality is an image generation apparatus used to capture an image of a patient so as to generate a medical image. In the information system 120 according to the embodiment of the present invention, the radiographic system 100 including the X-ray source 101 and the FPD 102 corresponds to a modality. Here, "DX", which stands for digital radiography, is attached to the correction image as a modality tag (0008, 0060). When a moving image is captured, "RF", which stands for radio fluoroscopy, is attached. Furthermore, when the correction image is to be stored in the PACS 114, "1.2.840.10008.5.1.4.1.1.1.1", which represents a combination of a digital X-ray image of an object and storage of a service is attached as a SOP class UID tag (0008, 0016), which specifies a pair of a service and an object.

The display control module 215 controls content displayed on the monitor 106. The display control module 215 controls display of the patient information, the information on the imaging conditions, and the information on the state of the FPD 102 on the monitor 106. The information is displayed with the correction image on the monitor 106.

As another embodiment, the display control for causing the monitor 106 to display the correction image performed by the output control module 214 may be executed by the display control module 215. In this case, the display control module 215 causes the monitor 106 to display the captured radiation image or the correction image.

Note that some or all of the components included in the controller 105 may not be fixed in the controller 105 and may be realized as an image processing system included in the information system 120. For example, an image processing apparatus which executes an image processing program including the image obtaining module 213, the output control module 214, and the image processing module 220 may be provided separately from the controller 105 which executes the imaging control module 211. Furthermore, the WS 113 may include some or all of the modules. The PACS 114 may include some or all of the modules. The FPD 102 may include a field-programmable gate array (FPGA) which realizes the functions of the image processing module 220. The components included in the controller 105 may be included in different apparatuses in an overlapping manner, and one of the apparatuses which performs processing may be selected in accordance with a user instruction. Furthermore, the components may be constituted by a work station, a server, and a storage device which are connected through a network, and the image processing according to the embodiment of the present invention may be performed through communication with these devices where appropriate.

Figure 3A:
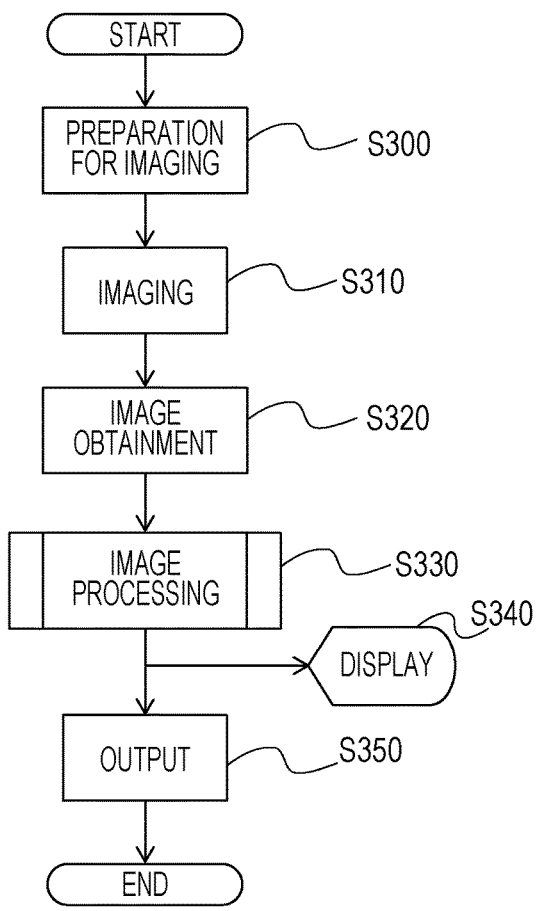
FIGS. 3A and 3B are flowcharts illustrating work flows performed when the image processing apparatus according to the embodiment of the present invention is used.
Figure 3B:
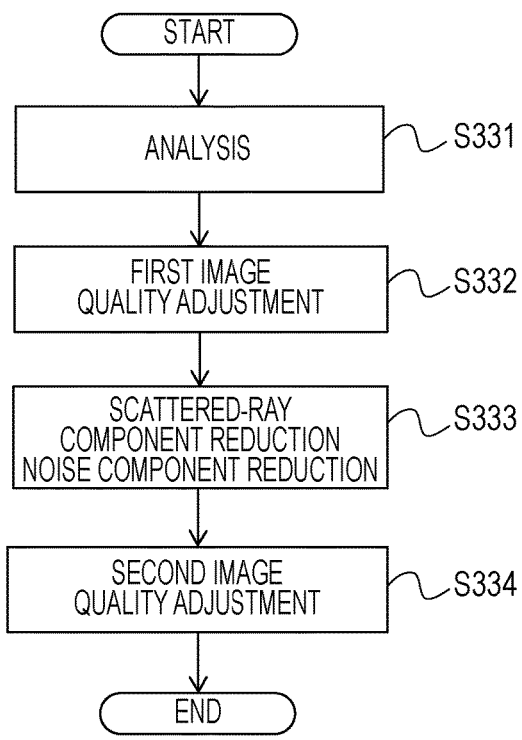

Next, a flow of imaging of a radiation image, image processing, and output performed by the radiographic system 100 and the information system 120 will be described with reference to FIGS. 3A and 3B. A main structure in which the processes of the modules may be realized is the CPU 201 or the GPU 208 in processing below, unless otherwise stated.

In step S300, preparation for obtaining an X-ray image by irradiating the object 103 with an X-ray is performed. The imaging control module 211 reads the imaging order supplied from the RIS 112 and sets information on imaging conditions and information on parameters of the image processing. The high-voltage generation unit 104 is brought into a high-voltage pulse generation available state and the FPD 102 is brought into an imaging available state in accordance with the set information.

In step S310, imaging is performed to obtain an X-ray image. When the user presses an exposure switch (not illustrated) of the high-voltage generation unit 104, the X-ray source 101 irradiates the object 103 with an X-ray and the FPD 102 detects the X-ray. The X-ray which has reached the FPD 102 is converted into an electric signal so that data on an X-ray image is generated. A scattered-ray reduction grid (hereinafter referred to as a "grid") may be used for imaging to reduce the dose of the scattered ray which reaches the FPD 102.

In step S320, the controller 105 receives the data on the X-ray image from the FPD 102 via the image obtaining module 213 and obtains the X-ray image. The X-ray image is stored in the RAM 202 before being stored in the SSD 206.

In step S330, the image processing module 220 performs image processing on the X-ray image. A flow of the image processing will be described with reference to FIG. 3B.

In step S331, the image processing module 220 analyzes the X-ray image obtained in step S320. As a result of the analysis, imaging conditions and an imaging portion of the X-ray image are obtained, for example. The image processing module 220 may control the imaging control module 211 so as to obtain information on the imaging conditions and information on the imaging portion. Furthermore, the image processing module 220 generates a histogram representing the magnitude and frequency of the pixel signals through the analysis.

In step S332, the image processing module 220 performs a first image-quality adjustment process. The image processing module 220 performs a process of correcting variations of the characteristics of the fluorescent substance (not illustrated) of the FPD 102, a process of correcting defective pixels, a process of correcting blur caused by the FPD 102, and the like, for example. In a case where information indicating that the grid has been used for the imaging is obtained in step S331, the image processing module 220 performs image processing for reducing strips generated as a result of the grid. By this, in a case where the imaging is performed using the grid in step S310, strips generated as a result of the grid are prevented from being superposed on the obtained X-ray image. Note that parameters to be used for the first image-quality adjustment process may be determined in accordance with the information obtained in step S331 in addition to the information set in step S300.

A process in step S333 is performed by the scattered-ray estimation module 221 and the noise reduction module 222 which are included in the image processing module 220. The scattered-ray estimation module 221 estimates a scattered-X-ray component of a scattered X-ray which is included in the X-ray image and which is generated when the X-ray is scattered in the object 103. The noise reduction module 222 obtains first noise information from the X-ray image and second noise information from a scattered-X-ray reduction image in which the scattered-X-ray component estimated by the scattered-ray estimation module 221 is reduced in the X-ray image. Then the noise reduction module 222 reduces a noise component included in the X-ray. A process of the frequency processing module 223 may be also performed. The process in step S333 will be described later with reference to FIGS. 4 to 13.

In step S334, the image processing module 220 performs a second image-quality adjustment process. The image processing module 220 performs a gradation process, a dynamic range compression process, a frequency emphasis process, and the like in accordance with the histogram of the pixel values and the information on the imaging portion obtained in step S331, for example. Note that parameters to be used for the second image-quality adjustment process may be determined in accordance with the information obtained in step S331 in addition to the information set in step S300.

In step S340, the output control module 214 and the display control module 215 cause the monitor 106 to display an image which has been subjected to the image processing performed by the image processing module 220 in step S330 and to display information on the image. The user may perform an operation input for changing the parameters of the image processing where appropriate with reference to content of the display on the monitor 106. The process returns to step S330 where the image processing module 220 performs the image processing in accordance with the operation input associated with the change of the parameters, and the output control module 214 and the display control module 215 cause the monitor 106 to display content after the change in step S340.

In step S350, the image which has been subjected to the image processing performed by the image processing module 220 in step S330 to reduce the scattered-ray component and the noise component is output. For example, the output control module 214 outputs the correction image to the PACS 114 and the printer 116 via the NIC 204. By this, the PACS 114 stores the correction image, and the printer 116 outputs the correction image to a film or the like. The output control module 214 associates various information based on the DICOM standard with the image before outputting the information with the image in step S350.

The work flow using the radiographic system 100 is thus completed. The process from step S300 to step S320 may be performed in parallel to the image processing in step S330 and the display process in step S340, so that an X-ray image which is different from the X-ray image which has been subjected to the image processing is captured.

Next, the process of scattered-ray estimation and noise reduction executed by the controller 105, that is, the process in step S333 of FIG. 3B will be described with reference to FIG. 4. In a description below, the main structure which performs the process is the CPU 201 or the GPU 208, unless otherwise stated.

The image obtained through the radiography is formed by superimposing a scattered-X-ray image obtained from the scattered-X-ray scattered in the object 103 on a primary X-ray image obtained from a primary X-ray which is from the X-ray source 101 and has directly reached the radiation detecting elements (not illustrated) which constitutes the FPD 102. Furthermore, the X-ray image includes a so-called noise component caused by noise.

An output of the FPD 102, which is a digital X-ray imaging system, corresponds with the number of X-ray photons which are incident on the FPD 102 and with the energy of the X-ray photons. The noise in the digital X-ray imaging system may be broadly classified as electric noise of a radiation detector (not illustrated), structural noise due to a difference in detection efficiency between the radiation detecting elements (not illustrated), and quantum noise resulting from random characteristics of the X-ray photons. Of these types of noise, the electric noise and the structural noise are seen not to depend on the imaging radiation dose. The statistical distribution of the fluctuation of the X-ray photons is based on a Poisson distribution, and the quantum noise is seen to correlate with the number of X-ray photons which have reached the FPD 102. Furthermore, in a radiation dose in a case where the X-ray imaging is performed on a human body serving as an object, of the types of generated noise, quantum noise largely affects image quality.

In the image in which the scattered X-ray is reduced by the image processing, a component generated from the scattered X-ray is reduced in a signal component. However, the image has quantum noise in an amount which correlates with a radiation amount obtained by adding the primary X-ray and the scattered X-ray together. Accordingly, the scattered X-ray reduction image may give impression that the noise component is rather high to the signal component including structural information of the object to be observed. For example, the scattered X-ray reduction image may give the impression of a deteriorated rough graininess. Therefore, a reduction in the noise component in accordance with the amount of the scattered X-ray is seen to be effective. In general, a scattered-X-ray component included in an obtained radiation image is reduced by reducing the amount of scattered X-ray which reaches the FPD 102 by using a grid. Therefore, it is preferable that the image processing is performed on an X-ray image obtained without using the grid so that a scattered-X-ray component and a noise component are reduced in the X-ray image by the same amounts as in a case where an X-ray image is captured using the grid. A method for associating the amount of the scattered-X-ray component to be reduced in the image processing with the amount of the noise component to be reduced by the noise reduction process will be described hereinafter.

Figure 4:
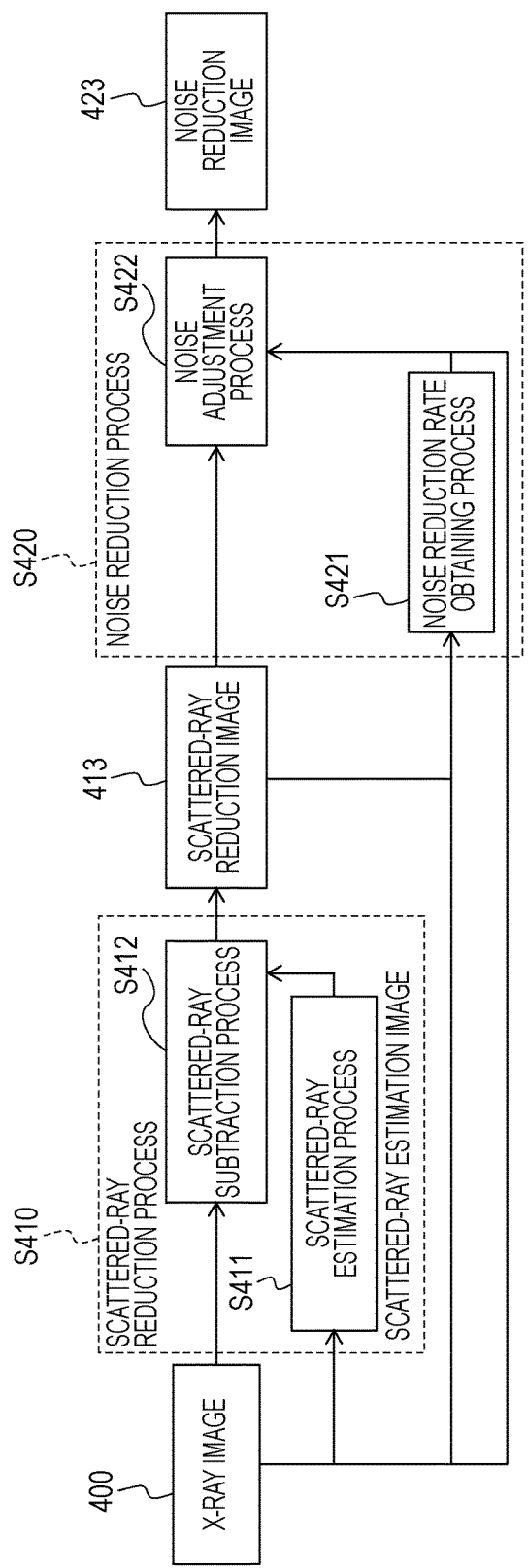
FIG. 4 is a block diagram illustrating a first embodiment of the present invention.

FIG. 4 is a diagram illustrating a flow of image processing according to the first embodiment. The image obtaining module 213 of the controller 105 obtains an X-ray image 400. In step S410, a scattered-X-ray component included in the X-ray image 400 is estimated and a scattered-ray reduction process is performed to reduce the scattered-X-ray component so as to obtain a scattered-ray reduction image 413. In step S420, a noise reduction process of reducing a noise component included in the X-ray image 400 is performed so as to obtain a noise reduction image 423. An image including a primary X component and a noise component which are equivalent to those of an X-ray image obtained by imaging using a grid is preferably obtained.

In the scattered-ray reduction process in step S410, a scattered-X-ray component included in the X-ray image 400 is estimated in step S411 and the scattered-X-ray component estimated in step S411 is reduced in the X-ray image 400 in step S412. The resultant scattered-ray reduction image 413 preferably has a primary X-ray signal amount corresponding to a signal amount of an X-ray image obtained using a grid.

The scattered-ray estimation process in step S411 employs a method below, for example. Assuming that the X-ray image 400 is denoted by "M", M is represented by a sum of the primary X-ray component denoted by "P", and the scattered-X-ray component denoted by "S". This is represented by Expression 1.

$$M = P + S \quad \text{Expression 1}$$

When an approximation formula representing the scattered-X-ray component S is represented by the primary X-ray component P, a scattered-ray component may be estimated by calculating Expression 1. Examples of the approximate formula which represents the scattered-X-ray component S by the primary X-ray component P include Expression 2 below.

$$S = -P \ln P * (G_1 + G_2) \quad \text{Expression 2}$$

Here, "$G_1$" and "$G_2$" denote Gauss functions for modeling an extension of the scattered X-ray. Furthermore, "*" denotes an operator of convolution. The scattered-X-ray component S may be estimated from the primary X-ray component P obtained from Expressions 1 and 2.

In the scattered-ray subtraction process performed in step S412, the scattered-X-ray component estimated in step S411 is subtracted from the X-ray image 400 so that the scattered-ray reduction image 413 is obtained. Here, the scattered-X-ray component may be subtracted in a desired ratio. By multiplying the scattered-X-ray component estimated in step S411 by a scattered-ray transmittance (JIS standard) of the grid and subtracting a resultant value from the X-ray image, an image including a primary X-ray component and a scattered-X-ray component which are equivalent to those of an image obtained by imaging using the grid may be obtained. This is represented by Expression 3.

$$V_{sr}(x,y) = R_p \cdot (V_{org}(x,y) - V_s(x,y)) + R_s \cdot V_s(x,y) \quad \text{Expression 3}$$

Here, "$V_{sr}(x, y)$" denotes a pixel value in a coordinate (x, y) of the scattered-ray reduction image 413, "$V_{org}(x, y)$" denotes a pixel value in a coordinate (x, y) of the X-ray image 400, and "$V_s(x, y)$" denotes a pixel value in a coordinate (x, y) of the scattered-X-ray component estimated in step S411. "$R_p$" denotes a transmittance of the primary X-ray and a value thereof may be fixed to 1. "$R_s$" denotes a transmittance of the scattered X-ray, and a scattered-ray transmittance of the grid based on the JIS standard is used. The user may adjust the value "$R_s$" where appropriate.

In the noise reduction process performed in step S420, a noise reduction rate obtaining process is performed in step S421 in accordance with first noise information obtained from the X-ray image 400 and second noise information obtained from the scattered-ray reduction image 413. Furthermore, in step S422, a noise adjustment process is performed in accordance with a noise reduction rate obtained in step S421. The resultant noise reduction image 423 preferably includes a noise component equivalent to that of an image captured using a grid.

Figure 5:
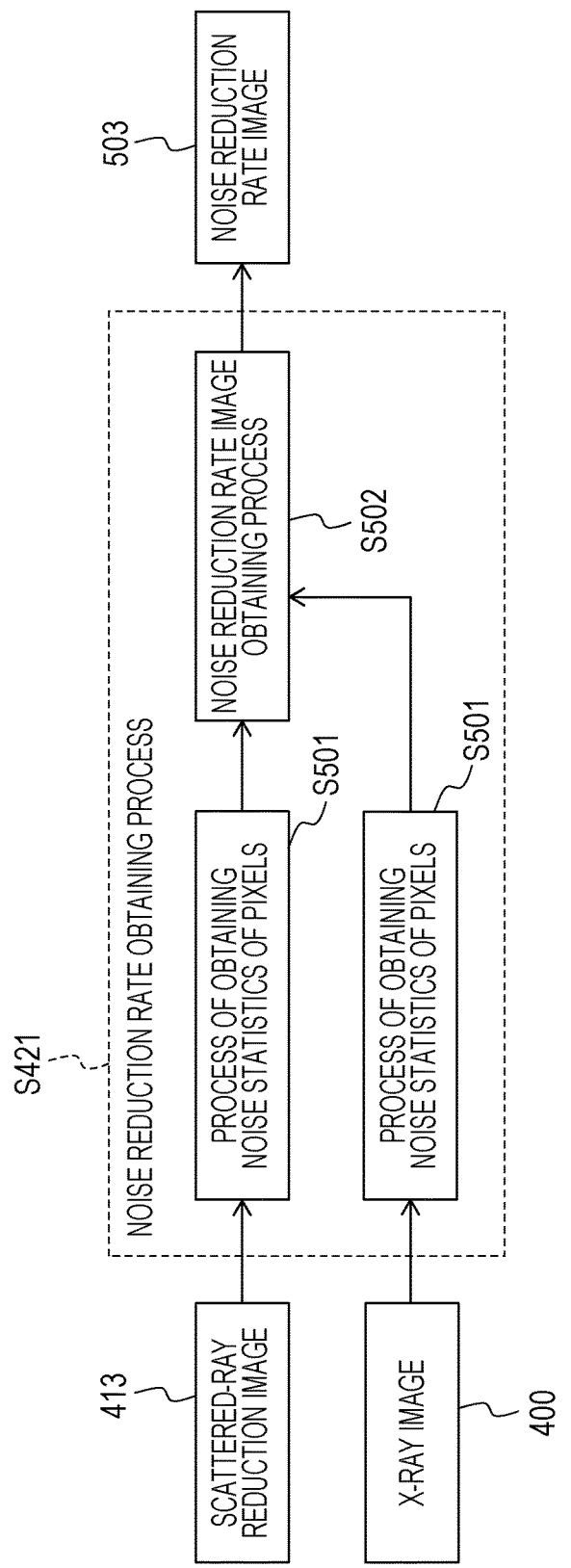
FIG. 5 is a block diagram illustrating the first embodiment of the present invention.

The noise reduction rate obtaining process performed in step S421 will be described with reference to FIG. 5. The noise reduction rate is a value serving as an index in the noise adjustment process in step S422. In step S501, a noise statistic obtaining process is performed on individual pixels. Specifically, first noise statistics are obtained from pixel values of the X-ray image 400 so that first noise information is obtained. Furthermore, second noise statistics are obtained from pixel values of the scattered-ray reduction image 413 so that second noise information is obtained. In step S502, a noise reduction rate image obtaining process is performed. Noise reduction rates serving as indices of noise reduction are obtained in accordance with rates of the second noise statistics to the first noise statistics so that a noise reduction rate image 503 which is an image of the noise reduction rate is obtained. As described above, in a case where the scattered-X-ray component is to be reduced by the image processing, although a component derived from the scattered X-ray is reduced in a signal component, an amount of quantum noise correlated with a radiation dose obtained by adding the primary X-ray and the scattered X-ray is included. The second noise statistics obtained from the pixel values of the scattered-ray reduction image 413 are not values indicating noise amounts included in the scattered-ray reduction image 413 but amounts of noise which may be generated due to a radiation dose which gives the pixel values or a radiation dose in which the scattered X-ray is reduced. Accordingly, rates of the second noise statistics to the first noise statistics serve as indices of noise reduction for a process of reducing a scattered-X-ray component.

In step S501, the noise statistic obtaining process is performed on the X-ray image 400 and the scattered-ray reduction image 413. The noise statistics are standard deviations based on the pixel values. Dispersion based on the pixel values may be used. As another example, the correlation between a value of a certain pixel and a noise statistic included in the certain pixel is stored in the SSD 206 in a form of a look-up table depending on a type of the radiation detector. Then the noise reduction module 222 reads the noise statistics from the look-up table to the RAM 202.

First, a noise standard deviation $\sigma_{org}(x, y)$ of the X-ray image 400 which is a first noise statistic is obtained from Expression 4.

$$\sigma_{org}(x,y) = \sqrt{\sigma_p(V_{org}(x,y)) + \sigma_{sys}} \quad \text{Expression 4}$$

Here, "$\sigma_p(v)$" indicates a standard deviation of quantum noise included in the certain pixel having a pixel value of v, and "$\sigma_{sys}$" indicates a standard deviation of system noise.

A noise standard deviation $\sigma_{sr}(x, y)$ of the scattered-ray reduction image 413 which is a second noise statistic is obtained from Expression 5.

$$\sigma_{sr}(x,y) = \sqrt{\sigma_p(V_{sr}(x,y)) + \sigma_{sys}} \quad \text{Expression 5}$$

In step S502, the noise reduction rate image obtaining process is performed. A noise reduction rate RNRR(x, y) indicates a rate of the second noise statistic to the first noise statistic. Specifically, the noise reduction rate RNRR(x, y) indicates a rate of the noise standard deviation $\sigma_{sr}(x, y)$ of the scattered-ray reduction image 413 corresponding to the primary X-ray component which is a target noise amount to the noise standard deviation $\sigma_{org}(x, y)$ of the X-ray image 400 which is a noise amount of an input image. RNRR(x, y) may be obtained using Expression 6.

$$RNRR(x, y) = \frac{\sigma_{sr}(x, y)}{\sigma_{org}(x, y)} \quad \text{Expression 6}$$

If $V_{sr}(x, y)$ is a scattered-X-ray reduction image corresponding to an image obtained by X-ray imaging using a grid as represented by Expression 3, a target noise amount may be equivalent to that of the image obtained by X-ray imaging using a grid.

Figure 6:
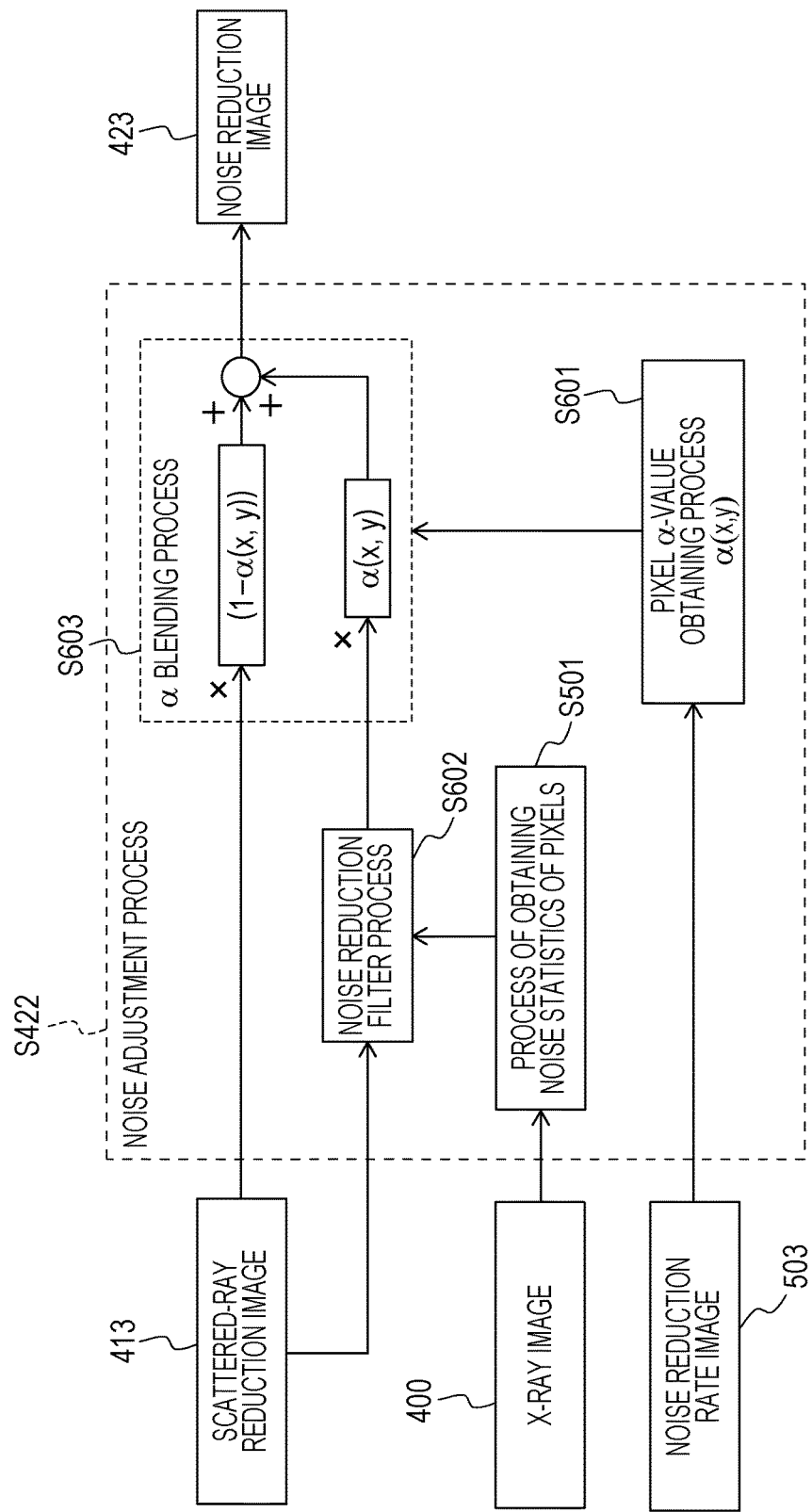
FIG. 6 is a block diagram illustrating the first embodiment of the present invention.

Next, the noise adjustment process performed in step S422 will be described with reference to FIG. 6. In the noise adjustment process, an amount of reduction of the noise component included in the X-ray image 400 is adjusted. By this, the noise reduction process suitably performed for different scattered-X-ray amounts generated in different portions may be realized.

In the noise adjustment process performed in step S422, first, in step S601, a pixel α value obtaining process of obtaining α values which are coefficients of weighting of the pixels from the noise reduction rate image 503 obtained based on the rates of the second noise statistics to the first noise statistics is performed. In step S602, image processing is performed on the first noise statistics obtained in step S501 and the scattered-ray reduction image 413 using a noise reduction filter. In step S603, an α blending process is performed to adjust a noise reduction amount using the scattered-ray reduction image 413, an image obtained by performing the image processing on the scattered-ray reduction image 413 using the noise reduction filter in step S602, and the α values which are the coefficients of the weighting of the pixels obtained in step S601. Detail description will be made hereinafter.

First, the α blending process performed in step S603 is represented as Expression 7.

$$V_{out}(x,y) = (1-\alpha(x,y)) \cdot V_{in}(x,y) + \alpha(x,y) \cdot V_{nr}(x,y) \quad \text{Expression 7}$$

Here, "$V_{out}(x, y)$" denotes a pixel value in a coordinate (x, y) of the noise reduction image 423. "$V_{in}(x, y)$" denotes a pixel value in a coordinate (x, y) of the scattered-ray reduction image 413. "$V_{nr}(x, y)$" denotes a pixel value in a coordinate (x, y) of the image obtained by performing the image processing on the scattered-ray reduction image 413 using the noise reduction filter. "α" denotes an α value which is a coefficient of the weighting of a pixel obtained in step S601. α is equal to or larger than 0 and equal to or smaller than 1.

Here, the α values of the pixels may be obtained by Expression 8 using the noise reduction rates.

$$\alpha(x, y) = \frac{RNRR(x, y) - 1}{R - 1} \quad \text{Expression 8}$$

Here, "α(x, y)" denotes an α value of a pixel, "RNRR(x, y)" denotes a noise reduction rate, and "R" denotes a noise reduction rate of the noise reduction filter.

A noise reduction rate R of Expression 8 uses a square-root of sum of squares of a filter coefficient in accordance with additivity of variance in a case where a noise reduction filter having linearity is used. On the other hand, a noise reduction rate obtained when a noise reduction filter is actually used for a certain image obtained by the FPD 102 may be used as a representative value in a case where a filter which does not have linearity is used.

Hereinafter, in the α blending process represented by Expression 7, a process of obtaining Expression 8 which is a relational expression of the noise reduction rates and the α values will be described.

First, when Expression 7 is described only for a noise component N(x, y) included in a pixel value V(x, y) of an image, Expression 9 below is obtained.

$$N_{out}(x,y) = (1-\alpha(x,y)) \cdot N_{in}(x,y) + \alpha(x,y) \cdot N_{nr}(x,y) \quad \text{Expression 9}$$

Here, "$N_{out}(x, y)$" denotes a noise component of the noise reduction image 423, "$N_{in}$" denotes a noise component of the scattered-ray reduction image 413, and $N_{nr}$ denotes a noise component of the image obtained by performing the image processing on the scattered-ray reduction image 413 using the noise reduction filter.

When the noise reduction rate of the noise reduction filter is denoted by R, Expression 8 is represented as Expression 10 in accordance with Expression 9.

$$N_{out}(x,y) = (1-\alpha(x,y)) \cdot N_{in}(x,y) + \alpha(x,y) \cdot R \cdot N_{in}(x,y) \quad \text{Expression 10}$$

Furthermore, when Expression 10 is solved for α(x, y), Expression 11 is obtained.

$$\alpha(x, y) = \frac{\frac{N_{out}(x, y)}{N_{in}(x, y)} - 1}{R - 1} \quad \text{Expression 11}$$

Here, "$N_{out}(x, y)/N_{in}(x, y)$" denotes a rate between a noise amount before the noise reduction and a noise amount after the noise reduction, and therefore, "$N_{out}(x, y)/N_{in}(x, Y)$" represents the noise reduction rate. When "$N_{out}(x, y)/N_{in}(x, y)$" is replaced by the target noise reduction rate RNRR(x, y), Expression 8 may be obtained. Specifically, the α values which are the coefficients for adjusting the noise reduction are obtained in accordance with the rates of the second noise statistics to the first noise statistics.

Next, a process in step S602 will be described. In step S602, the first noise statistics obtained in step S501 are used. This is because, in a case where the filter used in the noise reduction filter process obtains a threshold value of ε for a ε filter and weighting of a coefficient for pixels of nl-means, the noise statistics are required to be used.

In general, in the image processing using the noise reduction filter, a method for estimating statistic of noise such as quantum noise or electric noise in pixel values of an input image is employed. However, in this embodiment, the scattered-ray reduction image 413 obtained by changing pixel values of the X-ray image 400 by the scattered-ray reduction process performed in step S410 is used as an input image, it is difficult to estimate quantum noise included in the X-ray image 400 serving as an original image. Therefore, the first noise statistics are obtained from the X-ray image 400 and are used in the noise reduction filter. Note that this process may be omitted in a case where the noise reduction filter does not use noise statistics.

In step S602, the image processing is performed on the scattered-ray reduction image 413 using the noise reduction filter so that an image in which noise thereof is reduced at maximum is generated to be used for synthesis in the α blending process performed in step S603.

Examples of the noise reduction filter include a low-pass filter, a ε filter, a bilateral filter, and nl-means. If the noise reduction filter used for the X-ray image captured using the grid is used, noise may be reduced to an amount of noise of the X-ray image captured using the grid. However, even if a filter which is not precisely the same as the noise reduction filter is used, a noise amount which is similar to the noise amount obtained when the grid is used may be obtained when the filter has a noise reduction rate which is similar to a noise reduction rate of the noise reduction filter.

The α blending process performed in step S603 will lastly be described. In the α blending process, the noise reduction image 423 is obtained using the scattered-ray reduction image 413, the image in which noise thereof is reduced at maximum which is generated by the noise reduction filter process in step S602, and the α values of the pixels obtained in step S601. Specifically, the scattered-ray reduction image 413 and the image obtained by performing the image processing on the scattered-ray reduction image 413 using the noise reduction filter are combined with each other after pixels are weighted, so that a noise component included in the X-ray image 400 is reduced. Expression 7 above is used for the α blending process.

By the processing described above, the scattered-X-ray component included in the X-ray image 400 is estimated and the noise component is reduced in accordance with the first noise information and the second noise information so that a correction image in which the scattered-X-ray component and the noise component are reduced in the X-ray image 400 is obtained. The correction image is displayed on the monitor 106 by the output control module 214 and the display control module 215 and output to the PACS 114.

As represented by Expressions 4 and 5, the noise reduction rate RNRR serving as the index of the noise adjustment may not be obtained only using the scattered-X-ray component estimated in step S411, and an amount of noise reduction is not determined when the noise reduction is to be performed in accordance with the scattered-X-ray amount. However, appropriate noise reduction corresponding to an amount of the scattered X-ray which has reached the FPD 102 may be performed using the first noise information and the second noise information.

Second Embodiment

Next, a second embodiment of the present invention will be described. In the second embodiment, an image processing apparatus which allows a user to set an amount of noise reduction and which controls reduction of noise in an entire image based on the amount set by the user is illustrated. In general, a process of reducing a noise component and loss of a signal component are in the trade-off relationship, and as noise is reduced, a portion of a signal component is lost. A degree of tolerance of the trade-off varies depending on a purpose, for the user, of observation of a radiation image. Therefore, this embodiment is effective since the user may control an amount of noise reduction.

In general, a process of reducing a noise component and loss of a signal component are in the trade-off relationship, and as noise is reduced, a portion of a signal component is lost. A degree of tolerance of the trade-off varies depending on a purpose, for the user, of observation of a radiation image, and therefore, it is preferable that the user may control an amount of noise reduction.

Figure 7:
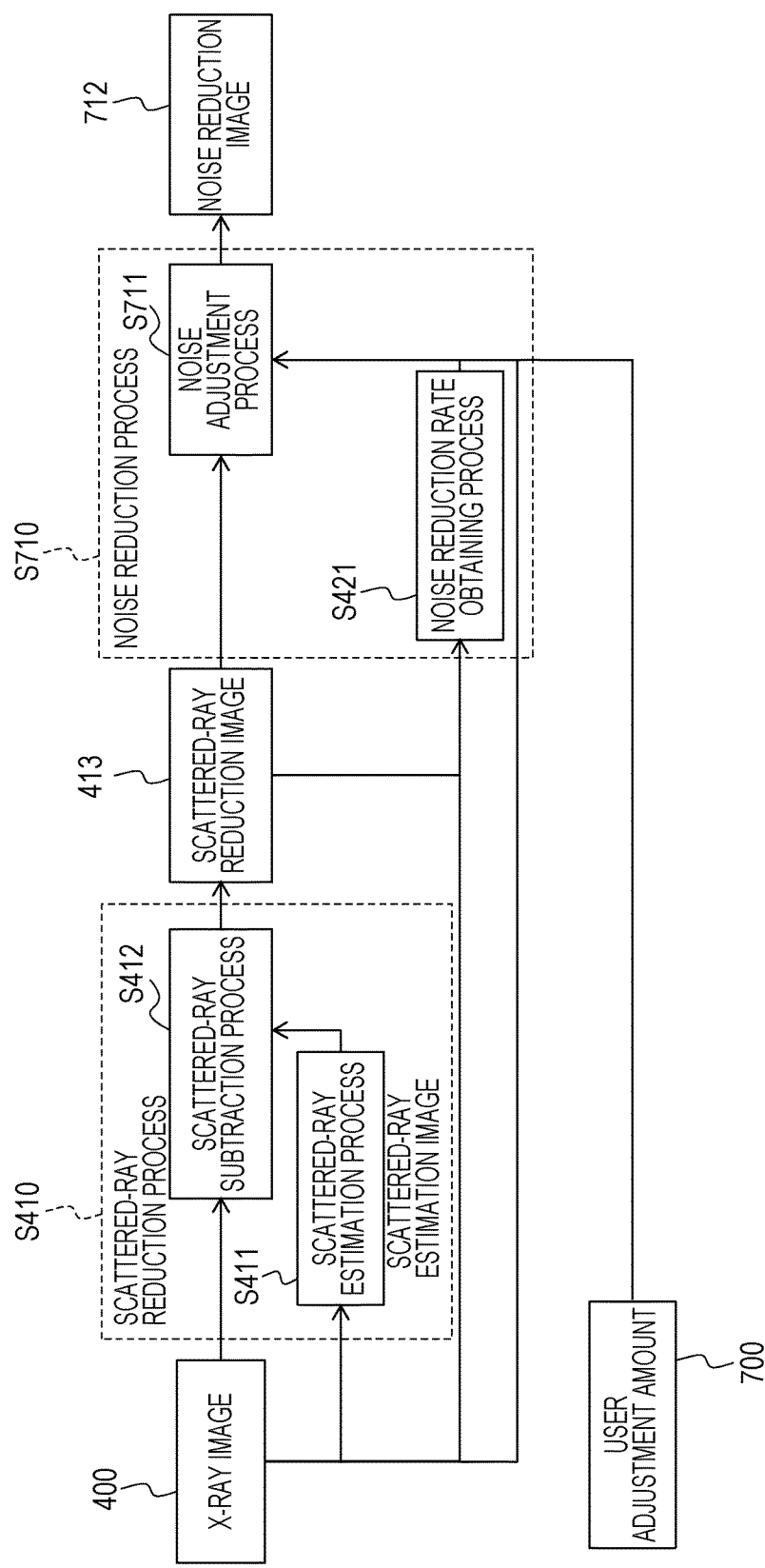
FIG. 7 is a block diagram illustrating a second embodiment of the present invention.

A flow of image processing according to the second embodiment will now be described with reference to FIG. 7. Detailed descriptions of components the same as those of the first embodiment are omitted. A user adjustment amount 700 is a value set by the user as a reference for adjusting noise reduction of an entire image. By a process the same as that of step S410, a scattered-X-ray component included in an X-ray image 400 is estimated and reduced so that a scattered-ray reduction image 413 is obtained. In step S710, a noise reduction process is performed based on the X-ray image 400, the scattered-ray reduction image 413, and the user adjustment amount 700. The user adjustment amount 700 is used for a noise adjustment process to be performed in step S711. A noise reduction image 712 is obtained via the noise adjustment process.

Figure 8:
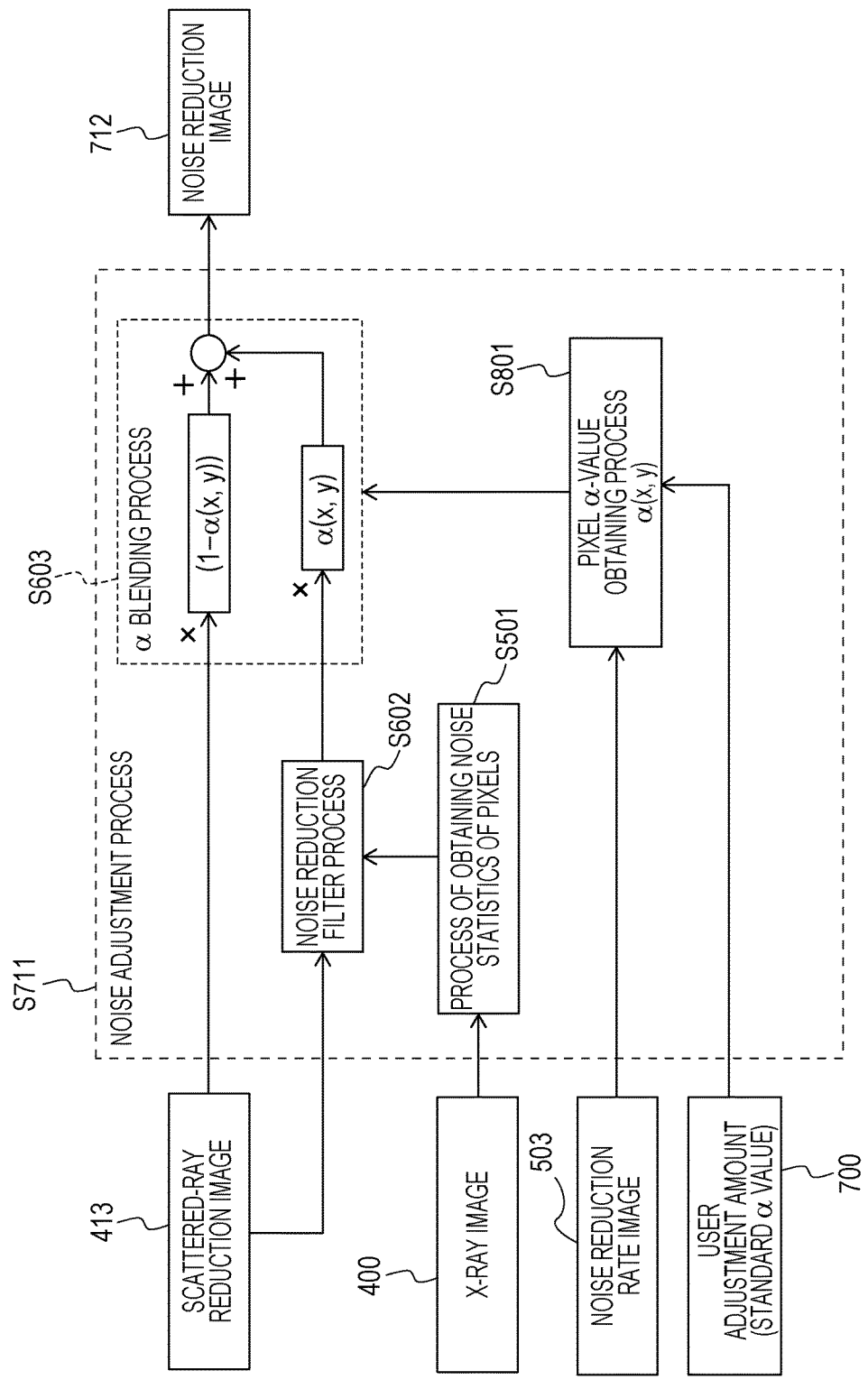
FIG. 8 is a block diagram illustrating the second embodiment of the present invention.

The noise adjustment process using the user adjustment amount 700 will now be described with reference to FIG. 8. In the noise adjustment process performed in step S711, first, an α-value obtaining process of obtaining α values of pixels using the noise reduction rate image 503 and the user adjustment amount 700 is performed in step S801. Furthermore, in step S501 which is the same as that of the first embodiment, first noise statistics are obtained from the X-ray image 400. In step S602 which is the same as that of the first embodiment, image processing using a noise reduction filter is performed on the scattered-ray reduction image 413 so that a noise reduction filter process is performed to generate an image in which noise is reduced at maximum. In step S603 which is the same as that of the first embodiment, an α blending process of adjusting a noise reduction amount in accordance with the scattered-ray reduction image 413, the image generated in step S602, and the α values of the pixels obtained in step S801 is performed.

Figure 9:
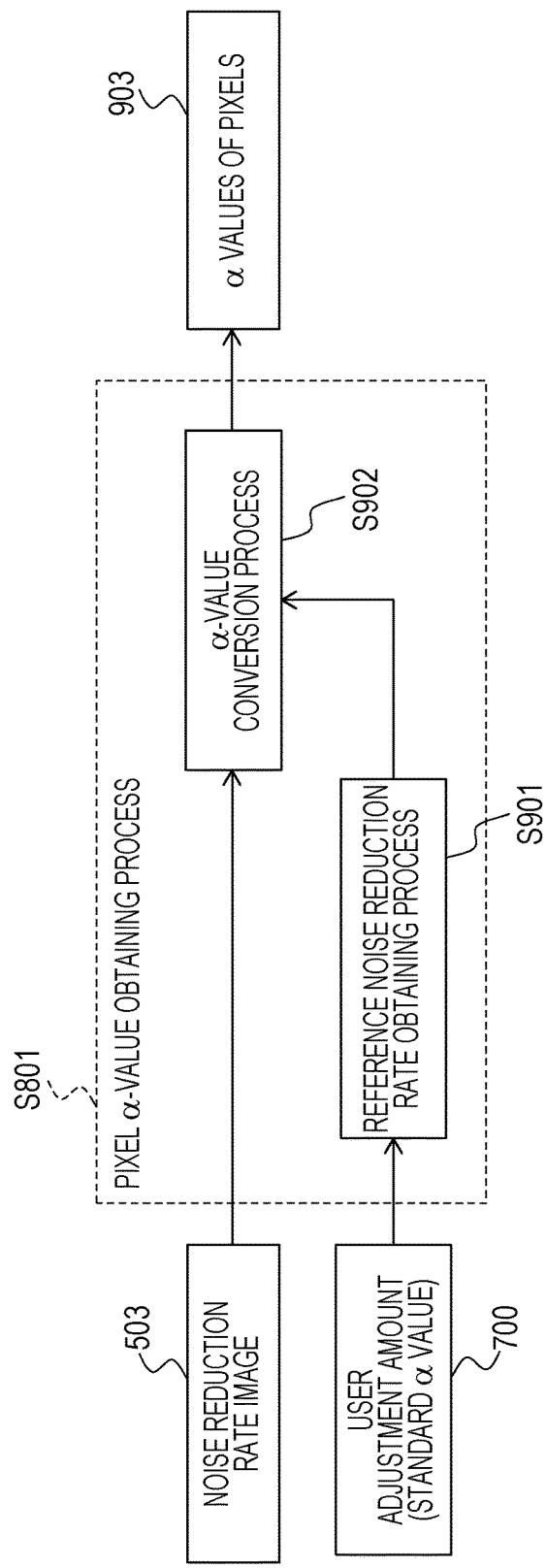
FIG. 9 is a block diagram illustrating the second embodiment of the present invention.

The pixel α-value obtaining process performed in step S801 will now be described with reference to FIG. 9. In the pixel α-value obtaining process, α values of the pixels to be used for the α blending process to be performed in step S603 are obtained in accordance with the noise reduction rate image 503 obtained via a process the same as that of the first embodiment and the user adjustment amount 700. The user adjustment amount 700 is a value serving as a reference of a noise adjustment amount of the pixels in the α blending process represented by Expression 8, for example. If noise reduction based on a scattered-X-ray amount is performed, a noise reduction amount of a pixel value corresponding to a portion in which a large amount of scattered-X-ray is generated is different from a noise reduction amount of a pixel value corresponding to a portion in which a small amount of scattered-X-ray is generated. To set a noise reduction amount desired by a user, α values are required to be set to individual pixels. However, the setting of α values to all the pixels is a burden for the user. Therefore, in step S801, a value $\alpha_N$ serving as a standard α value of the α blending is obtained as the user adjustment amount 700, and α values of individual pixels are obtained such that appropriate noise reduction is performed on the entire image when the value $\alpha_N$ is set as an α value in a certain pixel position.

In a process of obtaining α values of the pixels, first, in step S901, a reference noise reduction rate obtaining process of obtaining noise reduction rates of the individual pixels is performed using the user adjustment amount 700 as a reference. Furthermore, in step S902, an α-value conversion process of obtaining α values of the pixels in accordance with the noise reduction rate image 503 and the reference noise reduction rates obtained in step S901 is performed. The processes will be described in detail hereinafter.

In step S901, the value $\alpha_N$ serving as the standard α value is assigned to Expression 8 calculated to obtain noise reduction rates. This expression is represented as Expression 12 which obtains a reference noise reduction rate NNRR.

$$NNRR=(R-1)\cdot \alpha_N+1 \qquad \text{Expression 12}$$

In step S902, the α-value conversion process is performed to obtain α values of the entire image in accordance with the noise reduction rate image 503 and the reference noise reduction rates obtained in step S901. Specifically, the noise reduction rate image 503 is obtained based on rates of second noise statistics to first noise statistics and an α value which is a coefficient of weighting of a certain pixel of the X-ray image 400 is obtained as a standard α value by an operation input, and thereafter, the α values of the entire image, that is, weighting coefficients, are adjusted in accordance with the noise reduction rate image 503 and the standard α value, and noise reduction is performed in the following step.

In the α-value conversion process, a value obtained by multiplying a noise reduction rate RNRR(x, y) of Expression 8 by the reference noise reduction rate is determined as a final noise reduction rate. Accordingly, the α values of the pixels are represented by Expression 13.

$$\alpha(x, y) = \frac{NNRR \cdot RNRR(x, y) - 1}{R - 1} \qquad \text{Expression 13}$$

Note that, in a case where a value α(x, y) is larger than 1, 1 is set to the value α(x, y).

A pixel having the standard α value set by an operation input of the user preferably has a noise reduction rate RNRR(x, y) which is close to 1, that is, the pixel preferably corresponds to a portion in which an amount of generated scattered X-ray is small. This is because the standard α value is close to the final noise reduction rate. The pixel having the standard α value may be selected by an image processing module 220 in accordance with a value RNRR(x, y) which is a rate of a second noise statistic to a first noise statistic.

Other processes associated with the noise adjustment process are the same as those of the first embodiment, and therefore, descriptions thereof are omitted.

Accordingly, the user may control a noise reduction amount by an operation input, and the user may observe a desirable radiation image.

Third Embodiment

Next, a third embodiment of the present invention will be described. The third embodiment is different from the first and second embodiments in order of a scattered-ray reduction process and a noise reduction process. Although, as with the first and second embodiments, a purpose of the third embodiment is reduction of noise in accordance with an amount of a scattered X-ray which has reached an FPD 102, simpler processing may be performed in a case where a filter which requires noise statistics of a filter target image is used as a noise reduction filter.

Figure 10:
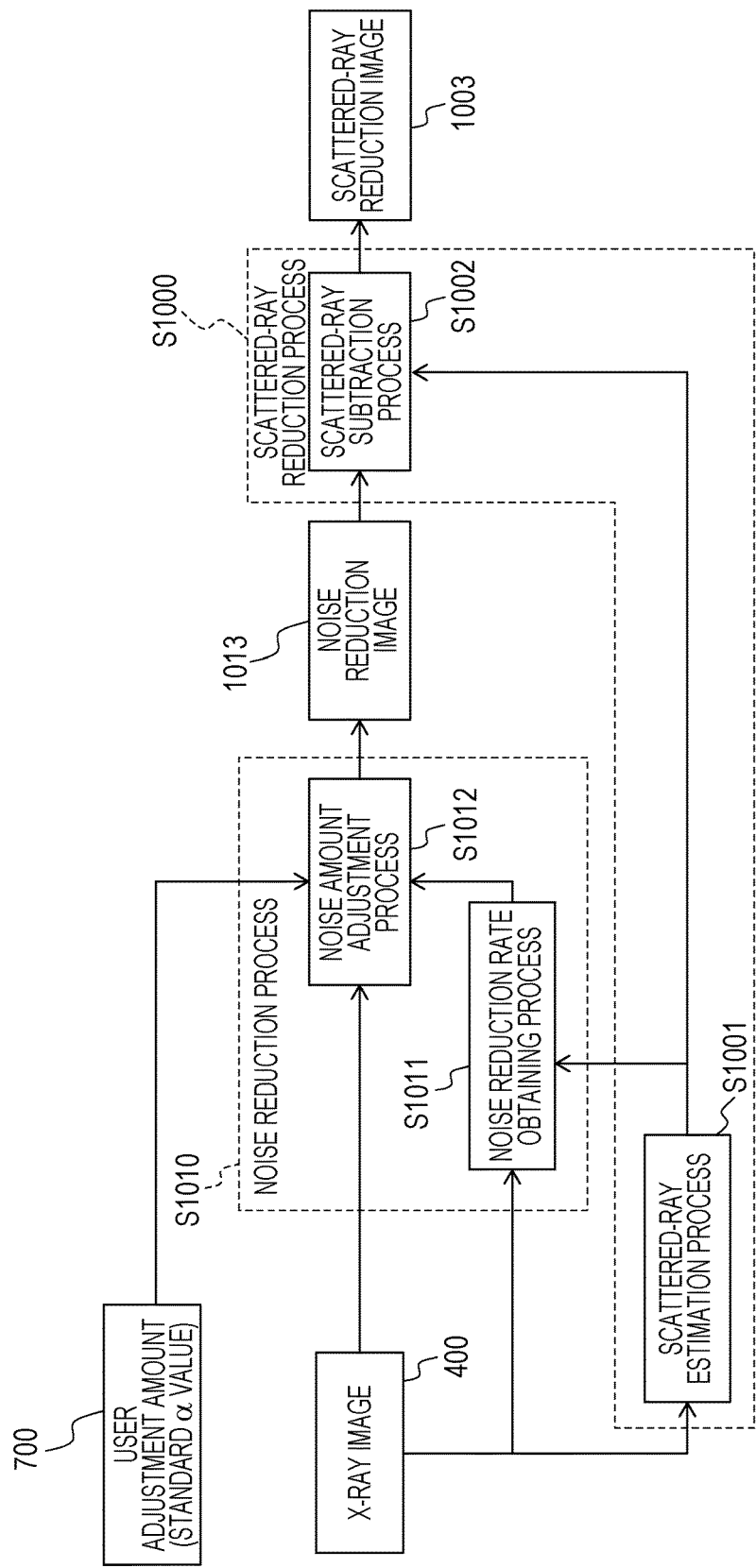
FIG. 10 is a block diagram illustrating a third embodiment of the present invention.

A flow of image processing according to the third embodiment will be described with reference to FIG. 10. An image obtaining module 213 of an image processing apparatus 105 obtains an X-ray image 400. In step S1001, a scattered-X-ray component included in the X-ray image 400 is estimated. In step S1010, a noise reduction process is performed in accordance with the scattered-X-ray component estimated in step S1001, the X-ray image 400, and a user adjustment amount 700 so as to obtain a noise reduction image 1013. In step S1002, a scattered-ray subtraction process of reducing the scattered-X-ray component from the noise reduction image 1013 based on the noise reduction image 1013 and the scattered-X-ray component estimated in step S1001 is performed so as to obtain a scattered-ray reduction image 1003.

Hereinafter, when processes the same as those of the first and second embodiments are performed, the descriptions described above are employed, and therefore, detailed descriptions thereof are omitted.

First, as with the first and second embodiments, a scattered-ray estimation process is performed in step S1001 so as to estimate a scattered-X-ray component included in the X-ray image 400.

Next, the noise reduction process in step S1010 will be described. First, in step S1011, a noise reduction rate obtaining process of obtaining noise reduction rates is performed in accordance with the X-ray image 400 and the scattered-X-ray component estimated in step S1001. In step S1012, a noise amount adjustment process is performed in accordance with the noise reduction rates obtained in step S1011, the X-ray image 400, and the user adjustment amount 700.

Figure 11:
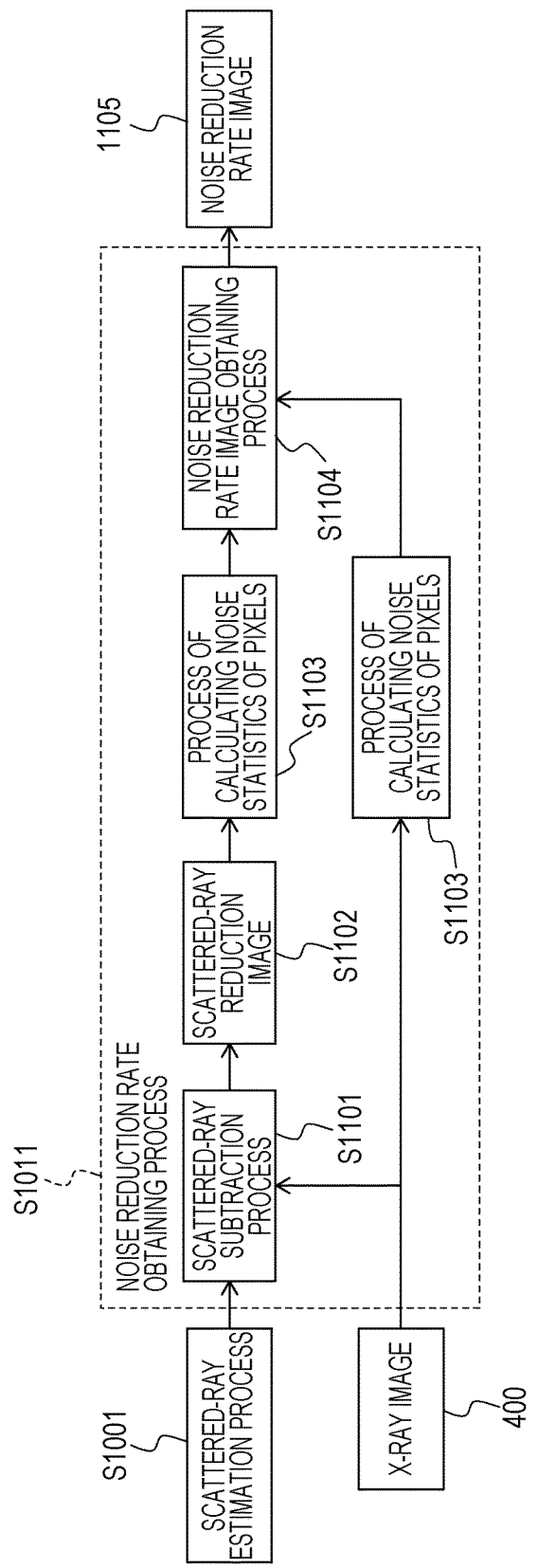
FIG. 11 is a block diagram illustrating the third embodiment of the present invention.

The noise reduction rate obtaining process of step S1011 will be described with reference to FIG. 11.

First, in step S1011, the scattered-X-ray component estimated in step S1001 is subtracted from the X-ray image 400 so that a scattered-ray reduction image 1102 is obtained. In step S1103, noise statistics of pixels of the X-ray image 400 and the scattered-ray reduction image 1102 are obtained. That is, first noise information and second noise information are obtained. In step S1104, a noise reduction rate image 1105 is obtained in accordance with rates of the second noise statistics to the first noise statistics. Next, a process in step S1011 will be described. Detailed descriptions of processes the same as those of the first and second embodiments are omitted.

In the scattered-ray reduction process in step S1101, a process the same as those of the first and second embodiments is performed so that the scattered-ray reduction image 1102 is obtained.

A process of obtaining noise statistics of the pixels in step S1103 is the same as those of the first and second embodiments. By this, a noise reduction rate image 1105 is obtained.

Figure 12:
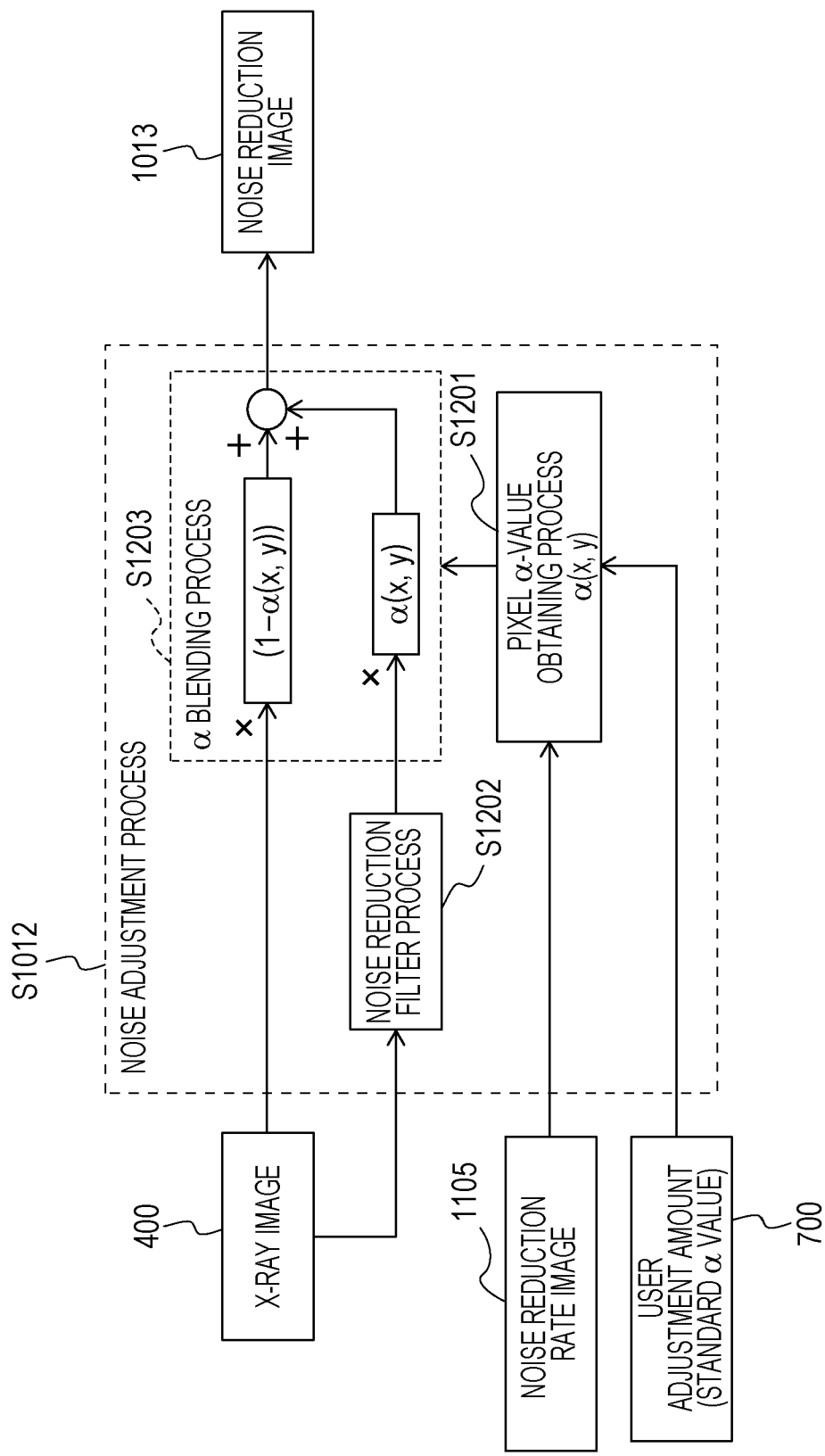
FIG. 12 is a block diagram illustrating the third embodiment of the present invention.

Next, the noise amount adjustment process in step S1012 will be described with reference to FIG. 12.

First, in step S1201, a pixel α-value obtaining process of obtaining α values which are coefficients of weighting of the pixels is performed in accordance with the noise reduction rate image 1105 and the user adjustment amount 700. In step S1202, a noise reduction filter process of obtaining an image by performing image processing using a noise reduction filter on the X-ray image 400 is performed. In step S1203, an α blending process of combining the X-ray image 400 and the image obtained in step S1202 with each other in accordance with the α values of the pixels obtained in step S1201 so that the noise reduction image 1013 is obtained is performed. These processes are described in detail hereinafter. Detailed descriptions of processes the same as those of the first and second embodiments are omitted.

The pixel α-value obtaining process in step S1201 is the same as that of the second embodiment.

In step S1202, the noise reduction filter used in the first and second embodiment is used. In the third embodiment, this process is image processing using the noise reduction filter performed on the X-ray image 400, and therefore, pixel values of the image subjected to the image processing may be uniquely associated with noise statistics included in the image. Therefore, the noise statistics of the pixels are not required to be obtained in advance, and the process of the third embodiment may be simplified.

In step S1203, the α blending process is performed in accordance with the image obtained by performing the image processing on the X-ray image 400 using the noise reduction filter, the X-ray image 400, and the α values of the pixels obtained in step S1201. As described above, although an input image of the α blending process is different from those of the first and second embodiments, a processing method is the same as those of the first and second embodiments.

Next, the scattered-ray subtraction process in step S1002 will be described. The scattered-X-ray component estimated in step S1001 is subtracted from the noise reduction image 1013 so that the scattered-ray reduction image 1003 is obtained. A subtraction method is the same as those of the first and second embodiments.

By this, the scattered-X-ray component and the noise amount corresponding to an amount of the scattered X-ray which has reached the FPD 102 may be reduced in the X-ray image 400. In step S1000 and step S1010, the noise reduction filter process is performed in accordance with a scattered-ray transmittance of a grid and a noise reduction rate of the grid, and an image including a primary X-ray component, a scattered-X-ray component, and a noise component which are equivalent to those of an X-ray image obtained by imaging using the grid is obtained. Furthermore, the noise statistics of the pixels are not required to be obtained in advance in step S1202, and therefore, a simplified process is attained.

Fourth Embodiment

Lastly, a fourth embodiment of the present invention will be described. In the fourth embodiment, a case where a noise reduction process is performed on components of a plurality of frequency bands in a divided manner will be described. A flow of other image processes may be the same as those of the first to third embodiments. Here, a case where the noise reduction process of step S1010 included in the flow of the image processing according to the third embodiment illustrated in FIG. 10 is performed on components in a plurality of bands in a divided manner will be described.

Figure 13:
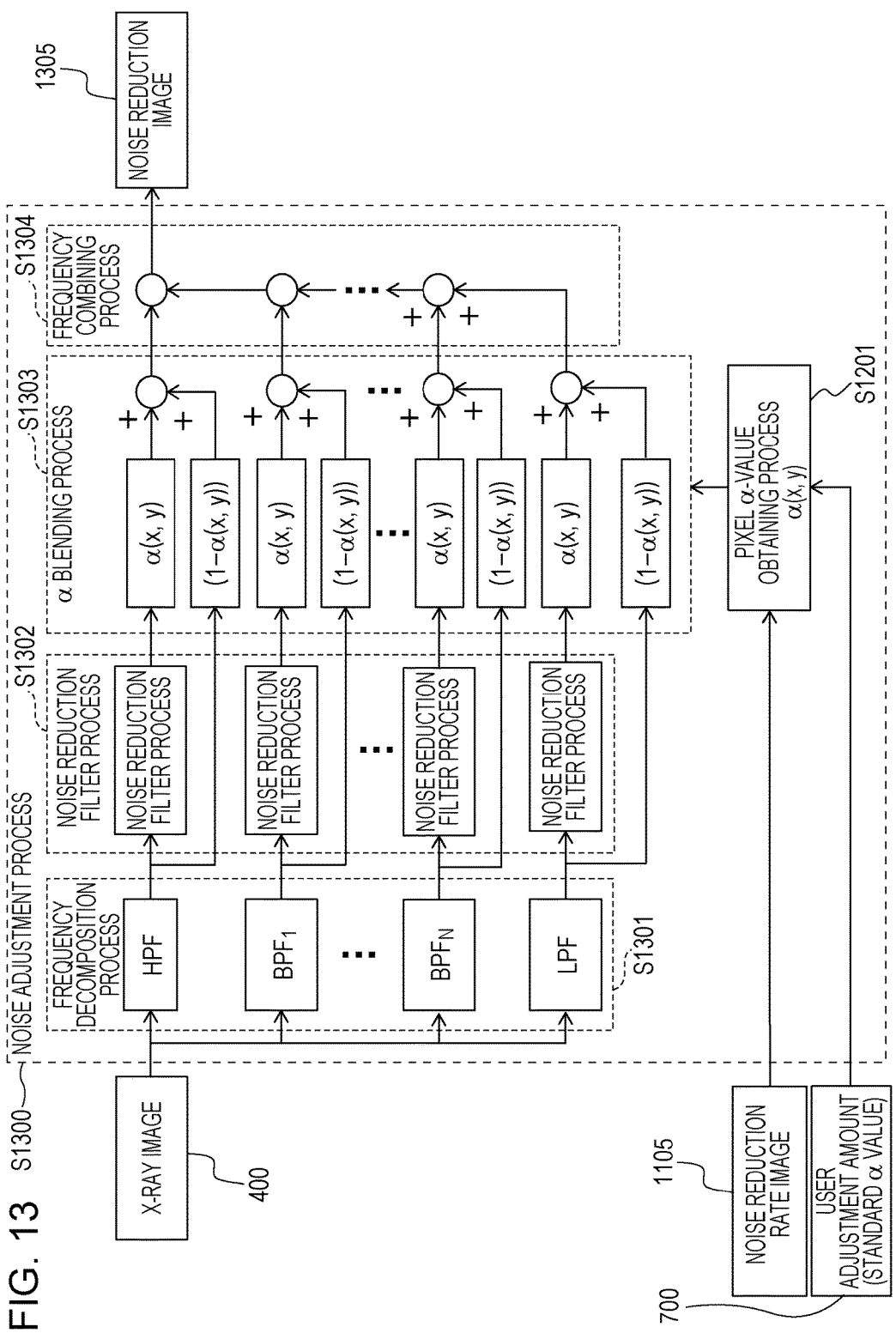
FIG. 13 is a block diagram illustrating a fourth embodiment of the present invention.

A noise adjustment process included in the noise reduction process according to the fourth embodiment will be described with reference to FIG. 13. In the noise adjustment process performed in step S1300, as with the third embodiment, a pixel α-value obtaining process of obtaining α values of pixels using a noise reduction rate image 1105 and a user adjustment amount 700 is performed in step S1201. In step S1301, a frequency processing module 223 performs a frequency decomposition process of resolving the X-ray image 400 into components of a plurality of frequency bands. In step S1302, the frequency processing module 223 performs a noise reduction filter process by performing image processing on the individual components of the plurality of frequency bands using the noise reduction filter. In step S1303, an α blending process of combining the components of the individual frequency bands which have been subjected to the image processing using the noise reduction filter and components of frequency bands of the X-ray image 400 with each other is performed. In step S1304, the components of the individual frequency bands which have been combined by the α blending process are further combined by a frequency combining process so that a noise reduction image 1305 is obtained.

The frequency decomposition process of step S1301 is performed by the frequency processing module 223. As illustrated in FIG. 13, the noise reduction image 1305 is obtained by performing the image processing using a high-pass filter (HPF), a plurality of band-pass filters corresponding to different frequency bands ($BPF_1$ to $BPF_N$), and a low-pass filter. As another method for performing the frequency decomposition, Laplacian pyramid decomposition or wavelet transform may be used.

In the noise reduction filter process in step S1302, the noise reduction filter which is the same as those of the first to third embodiments is used. The imaging process is performed on the components of the individual frequency bands using the noise reduction filter.

In the α blending process in step S1303, the components of the individual frequency bands of the X-ray image 400 are combined with the components of the frequency bands which have been subjected to the image processing using the noise reduction filter in step S1302 so that components of the frequency bands in which noise therein is reduced are obtained. By this, components in the individual frequency bands in which noise amounts thereof are adjusted are generated. A method for combining images in the α blending process is the same as those of the first to third embodiments.

In step S1304, the frequency processing module 223 combines the components of the individual frequency bands in which the noise amounts thereof are adjusted. The combining may be performed by adding the components of the individual frequency bands obtained in step S1303 in the individual pixels.

The scattered-ray reduction process in step S1000 may be performed, as with the foregoing embodiment, by resolving images into components of a plurality of frequency bands using the frequency processing module 223.

By this, an image in which the scattered-X-ray component and the noise amount corresponding to an amount of the scattered X-ray which has reached the FPD 102 are reduced in the X-ray image 400 may be obtained. Since the images are decomposed into the components of the plurality of frequency bands and the image processing using the noise reduction filter and the scattered-ray reduction process are performed on the components of the individual frequency bands, balance between a primary X-ray component and a scattered-X-ray component and a noise amount may be adjusted with higher accuracy.

Figure 14:
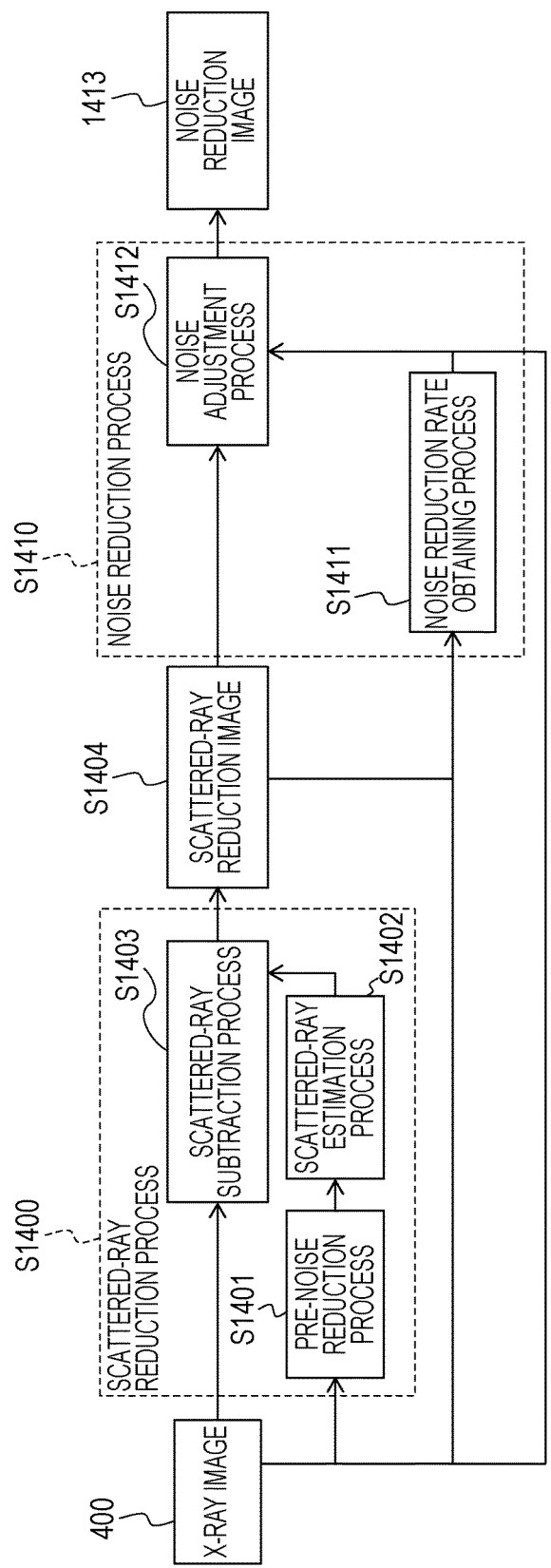
FIG. 14 is a block diagram illustrating image processing according to another embodiment of the present invention.

In the first to fourth embodiments, the scattered-ray estimation module 221 may perform a pre-noise reduction process so as to reduce the noise component of the X-ray image before the scattered-ray estimation process is performed. A case where the pre-noise reduction process is performed in the first embodiment will be described with reference to FIG. 14. The scattered-ray reduction process is performed in step S1400 in accordance with the X-ray image 400 obtained by the image obtaining module 213 so that a scattered-ray reduction image 1404 is obtained. In step S1410, a noise reduction process is performed in accordance with the X-ray image 400 and the scattered-ray reduction image 1404 so that a noise reduction image 1413 is obtained. Processes other than the pre-noise reduction process are the same as those of the first embodiments, and therefore, detailed descriptions thereof are omitted. The pre-noise reduction process is performed in step S1401 included in the scattered-ray reduction process. This is because, if noise is included in an image to be used in a scattered-ray estimation process, noise may be generated in an estimated image obtained as a result of the estimation process. The pre-noise reduction process is performed by the noise reduction module 222 under control of the scattered-ray estimation module 221. As a noise reduction method, a general noise reduction filter is used. Examples of the noise reduction filter include a ε filter, a lateral filter, and nl-means. Note that a determination as to whether the pre-noise reduction process is to be performed may be made by analyzing the X-ray image 400 which is an input image of the scattered-ray estimation process.

The noise reduction filter used in the first to fourth embodiments and the pre-noise reduction process will be described with reference to FIG. 15. Here, an ε filter is used as the noise reduction filter. As represented by Expression 14, a process is performed using the ε filter using $V_{in}(x, y)$ as an input image and an output image $V_{out}(x, y)$ is obtained.

$$V_{out}(x, y) = V_{in}(x, y) - \sum_{M=-m}^{m} \sum_{N=-n}^{n} a(N, M) \cdot f(V_{in}(x, y) - V_{in}(x + N, y + M))$$

Expression 14

Here, "n" denotes a size of the ε filter in an X direction and "m" denotes a size of the ε filter in a Y direction. Furthermore, "f(V)" denotes a function represented by Expression 15.

$$f(v) = \begin{cases} v & |v| \le \varepsilon \\ p & \text{otherwise} \end{cases}$$

Expression 15

In Expression 15, "p" may be determined in accordance with characteristics of a radiation detector (not illustrated). In an FPD 102, "p" is represented by Expression 16.

$$P = \varepsilon$$

Expression 16

Figure 15:
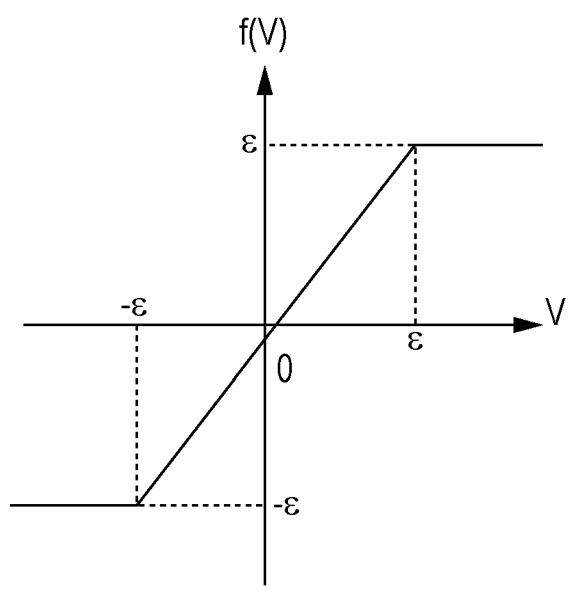
FIG. 15 is a diagram illustrating a noise reduction filter.

The function represented by Expression 15 is illustrated in FIG. 15.

Furthermore, "a(N, M)" is a coefficient used to store an average value of an image, and is set such that a sum thereof is 1 as represented by Expression 17.

$$\Sigma_{M=-m}^{m} \Sigma_{N=-n}^{n} a(N,M) = 1$$

Expression 17

The value a(N, M) may be a uniform value irrespective of values of N and M as long as Expression 17 is satisfied. Larger weighting may be applied as a position is closer to a center pixel (N=0, M=0) in a Gaussian distribution shape.

In the first to fourth embodiments, as the noise adjustment process, the image in which the noise component thereof is reduced at maximum using the noise reduction filter is combined with the scattered-ray reduction image or the X-ray image by the α blending process. However, as the process of adjusting the noise reduction amounts of the individual pixels, instead of the α blending process, a process of adjusting a noise reduction rate of the noise reduction filter for the individual pixels may be employed. When the ε filter described above is taken as an example, the value ε represented by Expression 16 may be determined in accordance with the noise reduction rate and noise standard deviation. Specifically, the value ε is set larger as the noise standard deviation is larger whereas the value c is set larger as the noise reduction rate is smaller.

In the first to fourth embodiments, an image intermediately generated, such as the noise reduction rate image 503, may be stored as display available data in the image processing. In this case, the user may perform desired image processing with reference to the intermediately-generated image. Furthermore, the intermediately-generated image may not be stored as a display available data. In this case, cost of the image processing may be reduced.

In the first to fourth embodiments, obtainment of an image including a primary X-ray component and a noise component which are equivalent to those of an X-ray image captured using a grid may be requested. In this case, the noise reduction rate of the noise reduction filter is approximated to the noise reduction rate in the case of using the grid. Furthermore, a scattered-X-ray transmittance and a primary X-ray transmittance of the grid are appropriately used in the step of generating the scattered-ray reduction image. Only the scattered-ray reduction image in which the scatted-X-ray component is reduced in the X-ray image may be displayed on the monitor 106 by the output control module 214 and the display control module 215. In this case, the user may easily input a user adjustment value which attains a noise reduction rate desired by the user with reference to the scattered-ray reduction image.

In the first to fourth embodiments, the noise reduction module 222 may perform control such that an amount of noise reduction is restricted in a specific case. As described above, reduction of a noise component and loss of a signal component are in the trade-off relationship. For example, an amount of noise reduction is restricted in accordance with the rates of the second noise statistics to the first noise statistics. Values of the rates are smaller as an amount of generation of the scattered-X-ray is larger. A threshold value is set for the values of the rates, and an amount of noise reduction is restricted in pixels having values of the rates smaller than the threshold value so that the noise component is not considerably reduced. Control is performed such that a difference amount between an α value of a pixel having a rate smaller than the threshold value and an α value of a pixel having a rate equal to the threshold value becomes smaller than a difference amount between an α value of a pixel having a rate larger than the threshold value and an α value of a pixel having a rage equal to the threshold value. Alternatively, in a case where a pixel having a value of a rate smaller than the threshold value is included in the scattered-ray reduction image, α values are set such that an amount of noise reduction is restricted in the entire image in the pixel α-value obtaining process of setting the α values of the entire image in accordance with a user adjustment amount. By this, the noise component is controlled so as not to be considerably reduced.

The present invention may be realized by a process of supplying programs which realize at least one function of the foregoing embodiments to a system or an apparatus through a network or a storage medium and reading and executing the programs using at least one processor included in the system or the apparatus. Furthermore, the present invention may be realized by a circuit (an ASIC, for example) which realizes at least one of the functions.

Although each of the image processing apparatuses according to the foregoing embodiments is a single apparatus, a mode in which the processing described above is executed by an image processing system in which apparatuses including a plurality of image processing apparatuses are combined in a communication available manner is also included in the present invention. Alternatively, the foregoing processing may be executed by a server apparatus which is shared by a plurality of modalities or a server group. In this case, the shared server apparatus corresponds to the image processing apparatuses according to the embodiments, and the server group corresponds to the image processing systems according to the embodiments. The plurality of apparatuses included in the information system 120 or the image processing system perform communication at least at a certain communication rate, and may not be installed in the same facility or the same country.

Furthermore, the present invention also includes a mode in which software programs which realize the functions of the foregoing embodiments are supplied to a system or an apparatus and a computer of the system or the apparatus reads and executes codes of the supplied programs.

Accordingly, the program codes which are installed in the compute to realize the processing of the embodiments by the computer is also included in the present invention. Furthermore, the functions of the foregoing embodiments are realized by a process of performing a portion or all of the actual processing using an OS or the like operating in the computer in accordance with instructions included in the programs read by the computer.

Embodiments obtained by appropriately combining the foregoing embodiments are also included in the present invention.

Accordingly, a noise amount corresponding to an amount of a scattered-ray which has reached a radiation detector may be reduced taking a noise component corresponding to a signal component of a scattered-ray reduction image into consideration by taking noise information obtained from a radiation image and noise information obtained from the scattered-ray reduction image into consideration.

Other Embodiments

Embodiments of the present invention can also be realized by a computer of a system or apparatus that reads out and executes computer executable instructions (e.g., one or more programs) recorded on a storage medium (which may also be referred to more fully as a 'non-transitory computer-readable storage medium') to perform the functions of one or more of the above-described embodiments and/or that includes one or more circuits (e.g., application specific integrated circuit (ASIC)) for performing the functions of one or more of the above-described embodiments, and by a method performed by the computer of the system or apparatus by, for example, reading out and executing the computer executable instructions from the storage medium to perform the functions of one or more of the above-described embodiments and/or controlling the one or more circuits to perform the functions of one or more of the above-described embodiments. The computer may comprise one or more processors (e.g., central processing unit (CPU), micro processing unit (MPU)) and may include a network of separate computers or separate processors to read out and execute the computer executable instructions. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2015-132179, filed Jun. 30, 2015, which is hereby incorporated by reference herein in its entirety.

What is claimed is:

1. An image processing apparatus comprising:
an estimation unit configured to estimate a scattered-ray component contained in a radiation image acquired by irradiating an object with a radiation, wherein the scattered-ray component originates from a scattered ray which is a radiation scattered in the object;
a noise reduction unit configured to reduce a noise component included in the radiation image in accordance with first noise information obtained from the radiation image and second noise information obtained from a scattered-ray reduction image obtained by reducing the scattered-ray component from the radiation image; and
an output unit configured to output a correction image obtained by reducing the scattered-ray component and the noise component in the radiation image.

2. The image processing apparatus according to claim 1, wherein the noise reduction unit obtains the first noise information from first noise statistics obtained from pixel values of the radiation image and obtains the second noise information from second noise statistics obtained from pixel values of the scattered-ray reduction image obtained by reducing the scattered-ray component estimated by the estimation unit in the radiation image.

3. The image processing apparatus according to claim 2, wherein the noise reduction unit reduces a noise component included in the radiation image in accordance with rates of the second noise statistics to the first noise statistics.

4. The image processing apparatus according to claim 3, further comprising an adjustment unit configured to adjust an amount of reduction performed by the noise reduction unit in accordance with the rates of the second noise statistics to the first noise statistics.

5. The image processing apparatus according to claim 4, wherein the adjustment unit restricts the amount of reduction performed by the noise reduction unit in a case where the rates are smaller than a predetermined value.

6. The image processing apparatus according to claim 1, further comprising an adjustment unit configured to adjust an amount of reduction performed by the noise reduction unit.

7. The image processing apparatus according to claim 1, wherein the noise reduction unit reduces a noise component included in the radiation image in accordance with an image obtained by performing image processing using a noise reduction filter on the scattered-ray reduction image and the scattered-ray reduction image.

8. The image processing apparatus according to claim 1, further comprising a frequency decomposition unit configured to decompose the scattered-ray reduction image into components of a plurality of frequency bands,
wherein the noise reduction unit reduces a noise component included in the radiation image in accordance with an image obtained by performing image processing using a noise reduction filter on the components of the plurality of frequency bands of the scattered-ray reduction image and combining the components of the plurality of frequency bands in which noise is reduced and the scattered-ray reduction image.

9. The image processing apparatus according to claim 8, wherein the noise reduction unit weighs and combines the components of the plurality of frequency bands in which the noise is reduced and the components of the plurality of frequency bands of the scattered-ray reduction image for individual pixels so as to reduce a noise component included in the radiation image.

10. The image processing apparatus according to claim 1, wherein the noise reduction unit reduces a noise component included in the radiation image in accordance with an image obtained by performing image processing using a noise reduction filter on the radiation image and the scattered-ray reduction image.

11. The image processing apparatus according to claim 10, wherein the noise reduction unit reduces the noise component included in the radiation image by weighting and combining the image obtained by performing the image processing using the noise reduction filter on the radiation image and the scattered-ray reduction image for individual pixels.

12. The image processing apparatus according to claim 1, further comprising a frequency decomposition unit configured to decompose the radiation image and the scattered-ray reduction image into components of a plurality of frequency bands,
wherein the noise reduction unit reduces a noise component included in the radiation image in accordance with the scattered-ray reduction image and an image obtained by performing image processing using a noise reduction filter on the individual components of the plurality of frequency bands of the radiation image and combining the components of the plurality of frequency bands in which noise is reduced.

13. The image processing apparatus according to claim 12, wherein the noise reduction unit reduces the noise component included in the radiation image by weighting and combining the components of the plurality of frequency bands in which noise is reduced and the components of the plurality of frequency bands of the scattered-ray reduction image for individual pixels.

14. The image processing apparatus according to claim 1, wherein a noise component included in the radiation image is reduced by weighting pixels of an image obtained by performing image processing using a noise reduction filter on the scattered-ray reduction image and pixels of the scattered-ray reduction image and combining the images for individual pixels.

15. The image processing apparatus according to claim 14, wherein the adjustment unit adjusts the weighting based on the rates.

16. The image processing apparatus according to claim 15, wherein the adjustment unit adjusts the weighting based on the rates and an operation input for determining a coefficient of weighting of a specific pixel included in the radiation image.

17. The image processing apparatus according to claim 15, wherein the adjustment unit determines the weighting based on the rates and an operation input for determining a coefficient of weighting of a specific pixel selected based on the rates, and adjusts an amount of reduction performed by the noise reduction unit such that a difference amount between a weighting coefficient of a pixel having a rate equal to a predetermined value and a weighting coefficient of a pixel having a rate smaller than the predetermined value is smaller than a difference amount between a weighting coefficient of a pixel having a rate equal to the predetermined value and a weighting coefficient of a pixel having a rate larger than the predetermined value.

18. The image processing apparatus according to claim 1, wherein the noise reduction unit has a function of obtaining noise information from pixel values and obtains the first noise information and the second noise information by the function.

19. An image processing method for an image processing apparatus, the image processing method comprising:
    estimating a scattered-ray component contained in a radiation image acquired by irradiating an object with a radiation, wherein the scattered-ray component originates from a scattered ray which is a radiation scattered in the object;
    reducing a noise component included in the radiation image in accordance with first noise information obtained from the radiation image and second noise information obtained from a scattered-ray reduction image obtained by reducing the scattered-ray component from the radiation image; and
    outputting a correction image obtained by reducing the scattered-ray component and the noise component in the radiation image.

20. An image processing system comprising:
    an estimation unit configured to estimate a scattered-ray component contained in a radiation image acquired by irradiating an object with a radiation, the scattered-ray component originating from a scattered ray which is a radiation scattered in the object;
    a noise reduction unit configured to obtain a noise reduction image by reducing a noise component included in the radiation image based on first noise information obtained from the radiation image and second noise information obtained from an image obtained by reducing the scattered-ray component in the radiation image; and
    an output unit configured to output a correction image obtained by reducing the scattered-ray component and the noise component in the radiation image.

21. A non-transitory computer-readable storage medium storing a program to cause an image processing apparatus to perform an image processing method, the image processing method comprising:
    estimating a scattered-ray component contained in a radiation image acquired by irradiating an object with a radiation, wherein the scattered-ray component originates from a scattered ray which is a radiation scattered in the object;
    reducing a noise component included in the radiation image in accordance with first noise information obtained from the radiation image and second noise information obtained from a scattered-ray reduction image obtained by reducing the scattered-ray component from the radiation image; and
    outputting a correction image obtained by reducing the scattered-ray component and the noise component in the radiation image.

* * * * *